(12) United States Patent
Kihira et al.

(10) Patent No.: US 7,231,318 B2
(45) Date of Patent: Jun. 12, 2007

(54) METHOD FOR PREDICTING DEGREE OF CORROSION OF WEATHER-RESISTANT STEEL

(75) Inventors: Hiroshi Kihira, Chiba (JP); Yasumori Fujii, Tokyo (JP); Yoshiyuki Harada, Chiba (JP); Takashi Kusunoki, Tokyo (JP); Norihito Fujikawa, Tokyo (JP); Hiroshi Takezawa, Tokyo (JP); Hiromichi Yasunami, Tokyo (JP); Kazumi Matsuoka, Chiba (JP)

(73) Assignee: Nippon Steel Corporation, Tokyo (JP)

( * ) Notice: Subject to any disclaimer, the term of this patent is extended or adjusted under 35 U.S.C. 154(b) by 0 days.

(21) Appl. No.: 10/483,504

(22) PCT Filed: Jul. 11, 2002

(86) PCT No.: PCT/JP02/07037

§ 371 (c)(1),
(2), (4) Date: Jan. 12, 2004

(87) PCT Pub. No.: WO03/006957

PCT Pub. Date: Jan. 23, 2003

(65) Prior Publication Data

US 2004/0176934 A1 Sep. 9, 2004

(30) Foreign Application Priority Data

Jul. 12, 2001 (JP) .......................... 2001-212764
Nov. 8, 2001 (JP) .......................... 2001-342763

(51) Int. Cl.
*G06G 7/48* (2006.01)

(52) U.S. Cl. .......................... 702/184; 702/30; 702/32; 703/2; 703/5; 703/12

(58) Field of Classification Search ........ 702/183–185, 702/22, 23, 24, 30–32, 25, 1, 3, 130, 136, 702/179, 181, 187; 703/5, 12, 6, 2; 324/700; 204/406, 407; 73/73, 77, 866, 170.16; 376/305; 422/7, 119; 428/471
See application file for complete search history.

(56) References Cited

U.S. PATENT DOCUMENTS 4,958,130 A * 9/1990 Mochizuki et al. ...... 205/776.5
6,544,659 B2 * 4/2003 Yamashita .................. 428/471
6,690,182 B2 * 2/2004 Kelly et al. ................. 324/700

FOREIGN PATENT DOCUMENTS

JP 07207340 8/1995

(Continued)

OTHER PUBLICATIONS

Translation of Nakamura et al., "Studies of Model for Predicting Corrosion Quantity of Ordinary Steel", 1981 (no month), pp. 158-159.*

(Continued)

*Primary Examiner*—Hal Wachsman
(74) *Attorney, Agent, or Firm*—Baker Botts LLP

(57) ABSTRACT

A predicted corrosion amount of a painted or unpainted atmospheric corrosion resistant steel is calculated by using extrinsic corrosion information including weather observation data, an amount of airborne salt, and an amount of sulfur oxide in a planned location for use where the atmospheric corrosion resistant steel is to be used, and intrinsic corrosion information on components of the atmospheric corrosion resistant steel. The weather observation data on this occasion preferably includes the annual wetness time, annual mean wind speed, and annual mean temperature. Moreover, it is preferable to calculate a corrosivity index, estimate a first-year corrosion amount of the atmospheric corrosion resistant steel and a rust stabilization index from the corrosivity index, and calculate a corrosion amount accumulated over time.

10 Claims, 26 Drawing Sheets

FOREIGN PATENT DOCUMENTS

| | | |
|---|---|---|
| JP | 07242993 | 9/1995 |
| JP | 11071632 | 3/1999 |
| JP | 11172370 | 6/1999 |
| JP | 2000001816 | 1/2000 |

OTHER PUBLICATIONS

Translation of Nakamura et al., "Study of Model for Predicting Corrosion Weight Loss of Atmospheric Corrosion Reistant Low-Alloy Steel", 1982 (no month), Metal Surface Technology, vol. 3, No. 2, pp. 29-34.*

Translation of Kitase et al., "The Corrosive Characteristics of Horizontally Exposed Metal Plates at the Inside of a Screen", 1995 (no month), Report of Nagoya Environmental Science Research Center, No. 25, pp. 1-13.*

Translation of Ishihara et al., "Research Relating to Corrosion Resistance of Metal Materials and Rustproof Coating Materials in Okinawa Prefecture (Part 4) Results of 2-Year Atmospheric Exposure Testing", Chukoshi Kenkyu Hokoku No. 20, 1992, pp. 51-61.*

Translation of Tsujino et al., "The Impact of Acid Deposition on Copper in China", 1998 (no month), Journal of Shindo Technology Research Council, vol. 37, pp. 86-93.*

Translation of "Report of Joint Research on Application of Weatherproof Steel Materials in Bridges (X)", Dec. 1989, Kyoto Kenkyu Hokoku, No. 30, pp. 1-70.*

Motoharu Nakamura et al., Dai 64 kai Gakujutsu Koen Taikai Yoshishu, pp. 158 to 159 (1981) (no month.

Motoharu Nakamura et al., Konjoku Hyomen Gijutsu, vol. 33, No. 2, pp. 77 to 82 (1982) (no month.

Kanemori Ishihara et al., Okinawa-Ken Kogyo Shikenjo Kenkyu Hokoku, No. 20, pp. 51 to 61 (1992) (no month.

Yoshio Tsujino et al., Shindo-Gijutsu Kenkyukaishi, vol. 37, pp. 86 to 93 (1998) (no month.

Yoshio Tsujino et al., Dai 45 Kai Proceedings of JSCE Materials and Environments, pp. 375 to 376 (1998) (no month.

Suguru Kitase et al., Annual Report Nagoya City Environmental Science Research Institute, No. 25, pp. 47 to 51 (1995) (no month.

Ministry of Construction Public Works Research Institute, Editied by Shadan Hojin Kozai Kurabu & Japan Association of Steel Bridge Construction, "Taikosei Kozai no Kyoryo eno Tekiyo ni Kansuru Kyodo Kenkyu Hokokusho (X)—Bakuro Shikenhen no Dai 3 Kai oyobi Dai 4 Kai Fushokuryo Chosa Kekka—Heisei 1 nen (1989)", pp. 1 to 63.(no month.

Patent abstract of Japanese Publication No. 08134587, dated May 28, 1996.

Patent abstract of Japanese Publication No. 02125839, dated May 14, 1990.

Patent abstract of Japanese Publication No. 05051668, dated Mar. 2, 1993.

V. Kucera, J. Tidblad, A.A. Mikhailov [ISO/TC156/WG4-N314 Annex A], Mar. 30, 1990, Abstract, p. 2, 4, 6, 8, 10, 12, 14, 16.

Nakamura et al., "Study Of Model For Predicting Corrosion Weight Loss Of Plain Steel," The Surface Finishing Society Of Japan, Executive Summary of 64th Academic Lecture Meeting, pp. 158-159, Sep. 1981.

Nakamura et al., "Study of Model For Prediciting Corrosion Weight Loss Of Atmospheric Corrosion Resistant Low-Alloy Steel," Konjoku Hyomen Gijutsu, vol. 33, No. 2, pp. 77-82, 1982 (no month/.

Ishihara et al., Okinawa-Ken Kogyo Shikenjo Kenkyu Hokoku, No. 20, pp. 51-61, 1993. (no month/.

Tsujino et al., "The Impact of Acid Deposition On Copper in China," Shindo Gijutsu Kenkyukaishi, vol. 37, pp. 86-93, 1998.(no month.

Tsujino et al., Dai 45 Kai Proceedings of JSCE Materials and Environments, pp. 375-376, 1998, (no month/.

"New Development Of Ruse Science To Realize Minimum Maintenance Bridge Concept," Japan Society Of Corrosion Engineering, Rust Science Workshop, p. 9. 1-7, Jun. 25, 2001.

"Collaborative Report On Application Of Atmospheric Corrosion Resistant Steel To Bridges (XV)," Public Works Research Institute Of The Ministry Of Construction, The Kozai Club, Japan Association Of Bridge Construction, p. 20-25, Mar. 1992.

Kihira et al., "Creation of Alloy Design Concept for Anti Air-Born Salinity Weathering Steel," Zairyo-To-Kanyko, vol. 49, No. 1, pp. 30-40, 2000.

* cited by examiner

PRIOR ART

| EAST LONGITUDE/NORTH LATITUDE INPUT | | | | | |
|---|---|---|---|---|---|
| | DEGREE | MINUTE | SECOND | | DECIMAL CONVERSION VALUE OF FRACTIONS SMALLER THAN DEGREE |
| EAST LONGITUDE | 0 | 0 | 0 | = | 0.00000 |
| NORTH LATITUDE | 0 | 0 | 0 | = | 0.00000 |

RESULT TRANSFER

PARAMETER CALCULATION RESULT (ASSUMPTION OF BRIDGE INSIDE GIRDER)

◉ TO SECULAR PREDICTION (P)

TOKYO BAY COAST MODEL BRIDGE

CONDITION SETTING BY: HIROSHI KIHIRA

Nippon Steel Corporation
*Yosoku 2101*

[Next]

--- <V> VERTICAL CONDITION WITHOUT TREATMENT UNDER BRIDGE GIRDER ---

|  | 2K |  | 98% |  | EXCESSIVE INFLUENCE |  |
|---|---|---|---|---|---|---|
| VALUE A (SMA) | 0.009 |  | 0.025 |  | 0.025 |  |
| VALUE B (SMA) | 0.591 |  | 0.636 |  | 0.786 |  |
| VALUE A (3Ni-0.4Cu) | 0.005 |  | 0.014 |  | 0.014 |  |
| VALUE B (3Ni-0.4Cu) | 0.540 |  | 0.574 |  | 0.688 |  |

--- <H> HORIZONTAL CONDITION WITHOUT TREATMENT UNDER BRIDGE GIRDER ---

|  | 2K |  | 98% |  | EXCESSIVE INFLUENCE |  |
|---|---|---|---|---|---|---|
| VALUE A (SMA) | 0.012 |  | 0.036 |  | 0.036 |  |
| VALUE B (SMA) | 0.521 |  | 0.658 |  | 0.808 |  |
| VALUE A (3Ni-0.4Cu) | 0.007 |  | 0.020 |  | 0.020 |  |
| VALUE B (3Ni-0.4Cu) | 0.486 |  | 0.520 |  | 0.634 |  |

FIG. 17

SECULAR CORROSION AMOUNT PREDICTION OVERVIEW by Yosoku — Nippon Steel Corporation condition setting: HIROSHI KIHIRA

Yosoku 2101

<V> VERTICAL CONDITION UNDER BRIDGE GIRDER
(UNIT: mm/ONE SIDE)

| | 2% | 50% | 98% |
|---|---|---|---|
| 10 YEARS (SMA) | 0.034 | 0.071 | 0.108 |
| 50 YEARS (SMA) | 0.088 | 0.194 | 0.301 |
| 100 YEARS (SMA) | 0.132 | 0.300 | 0.468 |
| 10 YEARS (3Ni-0.4Cu) | 0.016 | 0.034 | 0.052 |
| 50 YEARS (3Ni-0.4Cu) | 0.039 | 0.085 | 0.130 |
| 100 YEARS (3Ni-0.4Cu) | 0.057 | 0.125 | 0.193 |

Graph(V-SMA)  Graph(V-3Ni)

<H> HORIZONTAL CONDITION UNDER BRIDGE GIRDRE
(UNIT: mm/ONE SIDE)

| | 2% | 50% | 98% |
|---|---|---|---|
| 10 YEARS (SMA) | 0.041 | 0.071 | 0.162 |
| 50 YEARS (SMA) | 0.095 | 0.194 | 0.468 |
| 100 YEARS (SMA) | 0.136 | 0.300 | 0.738 |
| 10 YEARS (3Ni-0.4Cu) | 0.021 | 0.034 | 0.065 |
| 50 YEARS (3Ni-0.4Cu) | 0.045 | 0.085 | 0.150 |
| 100 YEARS (3Ni-0.4Cu) | 0.064 | 0.125 | 0.215 |

Graph(H-SMA)  Graph(H-3Ni)

ATMOSPHERIC CORROSION RESISTANT STEEL USAGE ENVIRONMENT OVERVIEW

FILE (F)  DATA PROCESSING (P)  DISPLAY/SETTING (D)  EXPLANATION (Q)

REGION/SPOT: TOKYO BAY COAST M BRIDGE PORTION 2

EAST LONGITUDE (DECIMAL): 139.9883
NORTH LATITUDE (DECIMAL): 35.6833

PERSON WHO SETS CONDITIONS: HIROSHI KIHIRA

CONDITION FILE NAME: C:¥PROGRAM FILES¥YOSOKU¥41B CONDITION¥TOKYO BAY COAST M BRIDGE PORTION 2

OUTPUT FILE NAME: C:¥PROGRAM FILES¥YOSOKU¥41B CONDITION¥TOKYO BAY COAST M BRIDGE PORTION 2

Nippon Steel Corporation
*Yosoku 2101*

Input

ATMOSPHERIC CORROSIVITY (VALUE Z): 0.1359

NEIGHBORING WEATHERING STATION/WMO NUMBER: CHIBA 47682

ANNUAL MEAN TEMPERATURE (°C): 15.2
ANNUAL MEAN HUMIDITY (%RH): 72
WETNESS TIME (h/y): 3508.1
ANNUAL PRECIPITATION (mm): 1285.7
ANNUAL MEAN WIND SPEED (m): 4.3

AMOUNT OF AIRBORNE SALT (mg-NaCl/dm2/d)
☐ NATIONAL AVERAGE 0.015–0.17 mdd : 0.15

AMOUNT OF SULFUR OXIDE (mg-SO2/dm2/d)
☐ NATIONAL AVERAGE 0.0030–0.0090 mdd : 0.14

UNDER BRIDGE GIRDER

EXCESSIVE INFLUENCE DEGREE
A: 1.0
B: 0.15
std.

METHOD FOR PREDICTING DEGREE OF CORROSION OF WEATHER-RESISTANT STEEL

CROSS-REFERENCE TO RELATED APPLICATION(S)

This application is a national stage application of PCT Application No. PCT/JP02/07037 which was filed on Jul. 11, 2002, and published on Jan. 23, 2003 as International Publication No. WO 03/006957 (the "International Application"). This application claims priority from the International Application pursuant to 35 U.S.C. § 365. The present application also claims priority under 35 U.S.C. § 119 from Japanese Patent Application Nos. 2001-212764 and 2001-342763, filed on Jul. 12, 2001 and Nov. 8, 2001, respectively, the entire disclosures of which are incorporated herein by reference.

FIELD OF THE INVENTION

The present invention relates to a method for predicting an amount of corrosion of an atmospheric corrosion resistant steel, which is subjected to surface treatment such as rust stabilization treatment, painting or plating, and maintenance management such as inspection, repair or cleaning as required, and a method for selecting a steel type to which the aforementioned method is applied.

BACKGROUND OF THE INVENTION

Atmospheric corrosion resistant steels have been applied to many actual structures including bridges because of its unique property of preventing rust by rust. There are many cases where a reduction in maintenance management costs is attained by using this steel material with its functions utilized to the full. On the other hand, a problem sometimes arises when the atmospheric corrosion resistant steel is carelessly used in coastal regions and the like where there is a lot of airborne salt. In recent years, in inland regions as well, local formation of abnormal rust due to the spraying of thawing salt is sometimes found.

As is represented by the minimum maintenance bridge concept proposed by the Ministry of Land, Infrastructure and Transport of Japan, future structures including bridges are requested to employ atmospheric corrosion resistant steels, surface treatment technology, structural design methods, and the like which can be actually used reliably for a very long period while achieving a further reduction in maintenance and management costs. Therefore, as a form of 21st century type infrastructure which maintains and develops cost-competitiveness with Asian countries as our country as a whole, rust science study and application technology development related to the atmospheric corrosion resistant steel capable of realizing Life Cycle Cost ("LCC") minimum are greatly expected.

Against this background, in the Japan Society of Corrosion Engineering, the Rust Science Workshop which supports 21st century infrastructure was organized for four years from 1997. Many specialists enthusiastically discussed the concept of "stable rust" heretofore very confused as basic understanding to use atmospheric corrosion resistant steels more securely and safely.

As a result, the following suggestion has been issued as the opinion of the Society in the 132nd Corrosion Engineering Symposium sponsored by the Japan Society of Corrosion Engineering held on Jun. 25, 2001 (Japan Society of Corrosion Engineering, Rust Science Workshop: Reference materials for the 132nd Corrosion Engineering Symposium "New Development of Rust Science to Realize Minimum Maintenance Bridge Concept", p 3, Jun. 25, 2001).

"Rust stabilization" of the atmospheric corrosion resistant steel means a state in which the corrosion rate has reduced to the extent that the secular deterioration of the load carrying capacity of a structure is insignificant from an engineering viewpoint (0.01 mm/year or less as a standard).

As provisional interpretation: the stable rust is rust formed when rust on the atmospheric corrosion resistant steel is "stabilized". However, although the aforementioned state is defined as "rust stabilization", since the term of stable rust has a strong physical image, it is desirable to withhold the scientific use of this term. As an alternative material term, the term of protective rust is used for rust having a high protective function.

Rust when "stabilized" is characterized in that although a sufficient period (e.g., five years or more) has elapsed, the rust does not grow thick (except a case where traces of exfoliated rust are left).

One of the important messages in this suggestion is the definition of "rust stabilazation" of the atmospheric corrosion resistant steel. Namely, when the industrial material called an atmospheric corrosion resistant steel is used for a structure, the realization of "a rust stabilization state" in which the load carrying capacity of the structure using this material can exist stably over a long period is recognized anew as a higher objective concept than other various arguments about what the matter called stable rust is. Moreover, the development of the technology of predicting the accumulated amount of corrosion of the atmospheric corrosion resistant steel over a long period of time is suggested as one of the most important items in material selection, structural design, and maintenance/management.

Conventionally, among methods for predicting an accumulated corrosion amount of an atmospheric corrosion resistant steel over a long period of time which are generally performed, there is a method of performing an exposure test over a period of approximately ten years in a construction site or under atmospheric environmental conditions similar to those of the construction site, finding a value A and a value B by fitting a secular change of a corrosion loss obtained in this period to a relational expression of (amount of corrosion)=A×(exposure period)$^B$, and calculating a corrosion loss over any given long period of time with these values (see, for example, Public Works Research Institute of the Ministry of Construction, the Kozai Club, Japan Association of Steel Bridge Construction: Collaborative Research Report on Application of Atmospheric corrosion resistant steel to Bridges (XII), p 20, March, 1992).

However, in this predicting method, the exposure test in actual atmospheric environment over a period of approximately ten years is necessary to obtain constant terms, the value A and the value B, and funds, labor, and time are needed before a judgment is made. Hence, a problem that the market competitiveness of a technical business method adopted at present of the atmospheric corrosion resistant steel is weaker than that of concrete structures and the like which compete with the atmospheric corrosion resistant steel is indicated.

As for a flow concerning judgment on the applicability of the atmospheric corrosion resistant steel, flows such as shown in FIG. 1 to FIG. 4 are disclosed in Japanese Patent Laid-open No. 2000-1816 and so on. However, in each flow, only factors which contribute to the amount of corrosion in the usage environment are substantially arranged, and no quantitative criterion for judging the propriety of use of a steel type to be applied based on a predicted corrosion amount in an adaptive environment is proposed or disclosed. Namely, these flows are not effective solutions for a demand for a more quantitative judgment method based on the predicted corrosion amount. Moreover, these flows have a problem that the amount of sulfur oxide and the annual wetness time which are important parameters for the prediction of the corrosion amount are not considered at all.

In the conventional method for predicting long-term corrosion/wear of the atmospheric corrosion resistant steel, exposure test data in the construction site or exposure test data in an atmospheric environment similar to the construction site are indispensable, and to obtain the data, high expenses of test/analysis are needed. Further, regions where unpainted atmospheric corrosion resistant steels are used for road bridges in our country are limited to regions where the amount of airborne salt is 0.05 mdd or less (mdd is a brevity code of $mg/dm^2day$), but in some cases, abnormality does not occur to the atmospheric corrosion resistant steel even under the environmental condition of an airborne salt amount of 0.05 mdd or more. Therefore, there are some cases where an opportunity to reduce the maintenance cost is missed because the applicability is judged only with a single index. Furthermore, when the atmospheric corrosion resistant steel is used beyond the limit of application without sufficient prediction of corrosion/wear behavior, partial abnormal corrosion occurs, which causes unexpected repairing expenses.

As described above, no solution which associates corrosivity of environmental condition with rust stabilization performance of the atmospheric corrosion resistant steel exists, and hence it is said that the application of the atmospheric corrosion resistant steel entails high risks and high returns.

SUMMARY OF THE INVENTION

In view of the aforementioned situation, a technology has been researched for judging the applicability of an atmospheric corrosion resistant steel at low cost, speedily, and with high precision is indispensable. In addition, method has been reviewed for predicting a long-term corrosion loss of an atmospheric corrosion resistant steel by calculation based on weather data, airborne salt amount data, and sulfur oxide amount data in the vicinity of a construction site.

One of the objects of the present invention is to provide a method for predicting an amount of corrosion of an atmospheric corrosion resistant steel capable of solving the aforementioned problems of prior arts and judging the applicability of the atmospheric corrosion resistant steel at low cost, speedily, and with high precision.

As a result of a comprehensive research and study in order to solve the aforementioned problems, a natural phenomenon called the rust stabilization of an atmospheric corrosion resistant steel has been arranged, so as to construct a calculation technology philosophy of predicting a long-term corrosion/wear amount. Such calculation technology philosophy can be embodied in the form of software.

A method for predicting an amount of corrosion of an atmospheric corrosion resistant steel according to the present invention may include a calculation of a predicted corrosion amount of the atmospheric corrosion resistant steel using extrinsic corrosion information including weather observation data, an amount of airborne salt, and an amount of sulfur oxide in a planned location for use where the atmospheric corrosion resistant steel is to be used, and intrinsic corrosion information on components of the atmospheric corrosion resistant steel, with an electronic calculator.

A system for predicting a corrosion amount according to an exemplary embodiment of the present invention may include an input arrangement for receiving information. The system may also include a computing arrangement which is configured to calculate a predicted corrosion amount of an atmospheric corrosion resistant steel with extrinsic corrosion information including weather observation data, an amount of airborne salt, and an amount of sulfur oxide in a planned location for use where the atmospheric corrosion resistant steel is to be used, and intrinsic corrosion information on components of the atmospheric corrosion resistant steel which are received from the input arrangement. Further, the system according to the present invention can include an output arrangement which is adapted to output a result of the calculation by the computing arrangement.

The atmospheric corrosion resistant steel subject to the system and method of the present invention may includes a hot-rolled atmospheric corrosion resisting steel for welded structure (symbol: SMA) stipulated by JIS G 3114 and a super atmospheric corrosion resisting rolled steel (symbol: SPA-H, SPA-C) stipulated by JIS G 3125. Such steel can also includes an atmospheric corrosion resistant steel containing approximately 1–3 mass % of Ni, for example, as disclosed in Japanese Patent Application No. 5-51668, Japanese Patent Application No. 7-207340, Japanese Patent Application No. 7-242993, Japanese Patent Application No. 8-134587, Japanese Patent Application No. 11-71632, Japanese Patent Application No. 11-172370, the entire disclosures of which are incorporated herein by reference. The atmospheric corrosion resistant steel subject to the exemplary embodiments of the present invention also includes a coastal/seaside atmospheric corrosion resistant steel containing Mo, Cu. Ti, Cr, and so on, which has been recently developed.

The weather observation data is data obtained by observing weather conditions under which the atmospheric corrosion resistant steel is exposed. For example, the weather observation data may include data on an annual wetness time TOW (h), an annual mean temperature T (° C.), an annual mean wind speed W (m/sec.), and so on.

The amount of airborne salt is a value obtained by a particular method based on a method for measuring the amount of sea salt particles stipulated by Reference 3 of JIS Z 2381 (i.e., General requirements for outside exposure test method). In particular, a gauze which is dried well after thoroughly leaching out salt by pure water is folded in two and fitted into a wooden frame with an inside dimension of 100 mm×100 mm. Then, the gauze is exposed vertically for one month in a well-ventilated place which is not directly exposed to the rain, taken off after the exposure, and analyzed to find the amount of NaCl. The value obtained by expressing the amount of in NaCl in NaCl·$mg/dm^2$/day (brevity code: mdd) is the amount of airborne salt. On this occasion, attention needs to be paid to conversion into the amount of adhesion on one side. This data is widely used as an index indicating how much salt is contained in atmospheric environment such as a construction site and at what speed the salt adheres to a structure or the like.

An exemplary amount of sulfur oxide can be a value obtained by a particular method based on a method for measuring the amount of sulfur oxide stipulated by Reference 2 of JIS Z 2381 (i.e., General requirements for outside exposure test method). In particular, a cylinder made of plastic or the like, on which gauze coated with a lead dioxide paste is put, is exposed vertically for one month in a dedicated shelter. After the exposure, the cylinder is removed and analyzed. The value obtained by expressing the amount of $SO_2$ in $SO_2 \cdot mg/dm^2 day$ (brevity code: mdd) is the amount of sulfur oxide. This data is widely used as an index indicating how much sulfur oxide such as sulfur acid gas is contained in atmospheric environment such as a construction site and at what speed the sulfur oxide adheres to a structure or the like.

It should be understood that measurement values correlated with these values can be determined by methods other than JIS Z 2381, such as an ISO method and a direct measurement method of attached salt. If the measurement methods are different, the values may also differ according to a difference between their capture rates, but it should be understood that if the values are converted into an airborne salt amount and a sulfur oxide amount based on the aforementioned JIS method, the values can be applied to the method for predicting the amount of corrosion of the atmospheric corrosion resistant steel associated with the exemplary embodiments of the present invention.

The aforementioned exemplary method for predicting the amount of corrosion of the atmospheric corrosion resistant steel according to the present invention can be effectively performed by utilizing a computer to make the calculation. Therefore, as for the distribution thereof, the method according to present invention may be provided on a computer readable record medium, can also be downloaded from the medium via an electric communication line, such as the Internet.

An exemplary embodiment of a computer readable record medium according to the present invention may include a program thereon. The program can cause a computer to calculate a predicted corrosion amount with extrinsic information including weather observation data, an amount of airborne salt, and an amount of sulfur oxide in a planned location for use where an atmospheric corrosion resistant steel is to be used, and intrinsic corrosion information on components of the atmospheric corrosion resistant steel.

Further, the method of the present invention may be implemented by a computer. According to one exemplary embodiment of the method for selecting a steel type according to the present invention, a predicted corrosion amount of each of atmospheric corrosion resistant steels with extrinsic corrosion information can be calculated, including weather observation data, an amount of airborne salt, and an amount of sulfur oxide in a planned location for use where the atmospheric corrosion resistant steel is to be used, and intrinsic corrosion information on components of one or more than one type of atmospheric corrosion resistant steel planned to be used, by an electronic calculator. In addition, the predicted corrosion amount and a design permissible corrosion amount may be compared in a design life period using a calculating arrangement (e.g., an electronic calculator).

Another exemplary embodiment of a system for selecting a steel type according to the present invention can include an input which is configured to obtain information, and a computing arrangement which is programmed to calculate a predicted corrosion amount of each of atmospheric corrosion resistant steels with extrinsic corrosion information including weather observation data, an amount of airborne salt, and an amount of sulfur oxide in a planned location for use where the atmospheric corrosion resistant steel is to be used, and intrinsic corrosion information on components of one or more than one type of atmospheric corrosion resistant steel planned to be used which are inputted from the input means. Such exemplary system may also include a comparing arrangement which is adapted to compare the predicted corrosion amount and a design permissible corrosion amount in a design life period, and an output arrangement which can be adapted to output a result of the comparison.

Another exemplary embodiment of the method for maintaining and managing a steel structure according to the present invention may include the steps of: finding an actually measured first-year corrosion amount from an actual measurement result of a corrosion loss in any given period of an actual structure made of an atmospheric corrosion resistant steel or a corrosion loss in any given period of a vertical exposure member or a horizontal exposure member which is made of the atmospheric corrosion resistant steel and attached to the actual structure; predicting a corrosion amount of the atmospheric corrosion resistant steel with an electronic calculator with the actually measured first-year corrosion amount as $A_V$ or $A_H$; and determining a maintenance management policy based on the predicted corrosion amount of the atmospheric corrosion resistant steel.

Another embodiment of the method for maintaining and managing a steel structure according to the present invention includes the steps of: finding an actually measured first-year corrosion amount from an actual measurement result of a corrosion loss in any given period of an actual structure made of an atmospheric corrosion resistant steel or a corrosion loss in any given period of a vertical exposure member or a horizontal exposure member which is made of the atmospheric corrosion resistant steel and attached to the actual structure; calculating a corrosivity index Z by the undermentioned equation (Eq. 6) from extrinsic corrosion information including weather observation data, an amount of airborne salt, and an amount of sulfur oxide in a location where the actual structure is installed, and intrinsic corrosion information on components of the atmospheric corrosion resistant steel, with an electronic calculator; estimating a first-year corrosion amount of the atmospheric corrosion resistant steel from the corrosivity index Z with the electronic calculator; comparing the actually measured first-year corrosion amount and the estimated first-year corrosion amount with the electronic calculator; correcting the corrosivity index Z based on a result of the comparison with the electronic calculator; predicting a corrosion amount of the atmospheric corrosion resistant steel based on the corrected corrosivity index Z with the electronic calculator; and determining a maintenance management policy based on the predicted corrosion amount.

Another embodiment of the system for maintaining and managing a steel structure according to the present invention includes an input arrangement which can receive information, and a computing arrangement which is configured to respectively calculate actually measured first-year corrosion amounts of a vertical exposure member and a horizontal exposure member which are made of an atmospheric corrosion resistant steel based on actual measurement results of corrosion losses in any given period of the vertical exposure member and the horizontal exposure member made of the atmospheric corrosion resistant steel which are inputted from the input arrangement, calculating a predicted corrosion amount of the atmospheric corrosion resistant steel with extrinsic information including weather observation data, an amount of airborne salt, and an amount of sulfur oxide in a planned location for use where the atmospheric corrosion resistant steel is to be used which is received from the input arrangement, intrinsic corrosion information on components of the atmospheric corrosion resistant steel obtained via the input arrangement, and the respective actually measured first-year corrosion amounts, and determining a maintenance management policy based on the predicted corrosion amount.

An exemplary method for providing information on an atmospheric corrosion resistant steel according to the present invention includes the steps of: a user accessing a server for calculating a predicted corrosion amount of an atmospheric corrosion resistant steel with environmental data including weather observation data, an amount of airborne salt, and an amount of sulfur oxide, and intrinsic corrosion information on components of the atmospheric corrosion resistant steel from a terminal device via an electric communication line; the user inputting environmental data including weather observation data, an amount of airborne salt, and an amount of sulfur oxide in a planned location for use where an atmospheric corrosion resistant steel is to be used from the terminal device to the server; the user permitting the server to recognize intrinsic corrosion information on components of one or more than one atmospheric corrosion resistant steel planned to be used from the terminal device; the server calculating a predicted corrosion amount of each of the atmospheric corrosion resistant steels based on the environmental data and the intrinsic corrosion information; the server transmitting the predicted corrosion amount to the terminal device via the electric communication line; and the terminal device outputting the predicted corrosion amount.

An exemplary system for providing information on an atmospheric corrosion resistant steel according to the present invention may include a server, which is accessible to a user from a terminal device via an electric communication line, programmed to calculate a predicted corrosion amount of an atmospheric corrosion resistant steel with environmental data including weather observation data, an amount of airborne salt, and an amount of sulfur oxide, and intrinsic corrosion information on components of the atmospheric corrosion resistant steel, and to transmit the predicted corrosion amount to the terminal device via the electric communication line.

An exemplary method for an atmospheric corrosion resistant steel according to the present invention includes the steps of: a user accessing a server for calculating a predicted corrosion amount of an atmospheric corrosion resistant steel with environmental data including weather observation data, an amount of airborne salt, and an amount of sulfur oxide, and intrinsic corrosion information on components of the atmospheric corrosion resistant steel from a terminal device via an electric communication line; the user inputting environmental data including weather observation data, an amount of airborne salt, and an amount of sulfur oxide in a planned location for use where an atmospheric corrosion resistant steel is to be used from the terminal device to the server; the user permitting the server to recognize intrinsic corrosion information on components of one or more than one atmospheric corrosion resistant steel planned to be used from the terminal device; the server calculating a predicted corrosion amount of each of the atmospheric corrosion resistant steels based on the environmental data and the intrinsic corrosion information; the server transmitting the predicted corrosion amount to the terminal device of the user via the electric communication line; the terminal device outputting the predicted corrosion amount; and determining a business counterpart based on at least one type of element selected from the group consisting of the presence or absence of history of access to the server and the frequency of access to the server.

Another exemplary method for an atmospheric corrosion resistant steel according to the present invention includes the steps of: a user inputting extrinsic corrosion information including weather observation data, an amount of airborne salt, and an amount of sulfur oxide in a planned location for use where a customer plans to use an atmospheric corrosion resistant steel to an electronic calculator for calculating a predicted corrosion amount of an atmospheric corrosion resistant steel with extrinsic corrosion information including weather observation data, an amount of airborne salt, and an amount of sulfur oxide and intrinsic corrosion information on components of the atmospheric corrosion resistant steel; the user permitting an electronic arrangement to recognize intrinsic corrosion information on components of one or more than one type of atmospheric corrosion resistant steel which the customer plans to use; the electronic calculator calculating a predicted corrosion amount of each of the atmospheric corrosion resistant steels; and the user presenting a result of the calculation to the customer.

BRIEF DESCRIPTION OF THE DRAWINGS

FIG. 12 is a chart showing an example of a panel for setting conditions of long-term corrosion/wear prediction software for an atmospheric corrosion resistant steel;

FIG. 13 is a chart showing an example of a panel for obtaining longitude and latitude of the long-term corrosion/wear prediction software for the atmospheric corrosion resistant steel;

FIG. 15 is a chart showing an example of the panel for setting conditions of the long-term corrosion/wear prediction software for the atmospheric corrosion resistant steel the input to which is completed;

FIG. 16 is a chart showing an example of a panel displaying a first-year corrosion amount A and a rust stabilization index B of the long-term corrosion/wear prediction software for the atmospheric corrosion resistant steel;

FIG. 17 is a chart showing an example of a panel for viewing an overview of calculation results of the long-term corrosion/wear prediction software for the atmospheric corrosion resistant steel;

FIG. 23 is a chart showing an example of conditions provided to a usage environment conditions setting panel in a portion of a structure around which the amount of airborne salt is assumed to be relatively small in a bridge structure to be constructed;

FIG. 25 is a chart showing an example of conditions inputted to the usage environment conditions setting panel in a portion of the structure around which the amount of airborne salt is assumed to be relatively large and the humidity is assumed to be high in the bridge structure to be constructed;

DETAILED DESCRIPTION

Figure 1:
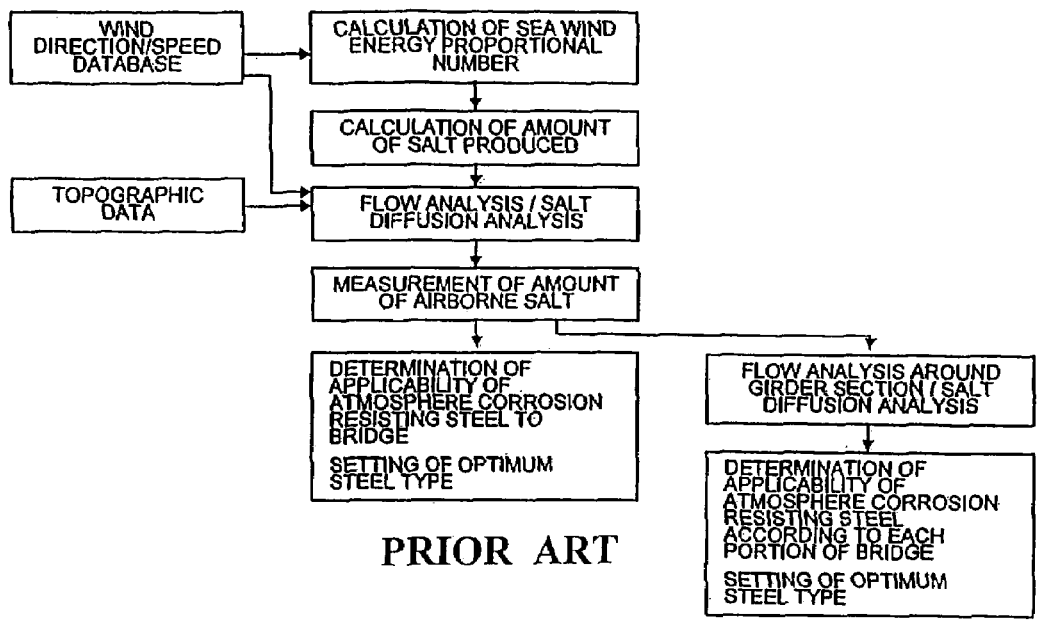
FIG. 1 is a flowchart showing an example of a conventional method for determining the applicability of an atmospheric corrosion resistant steel.
Figure 2:
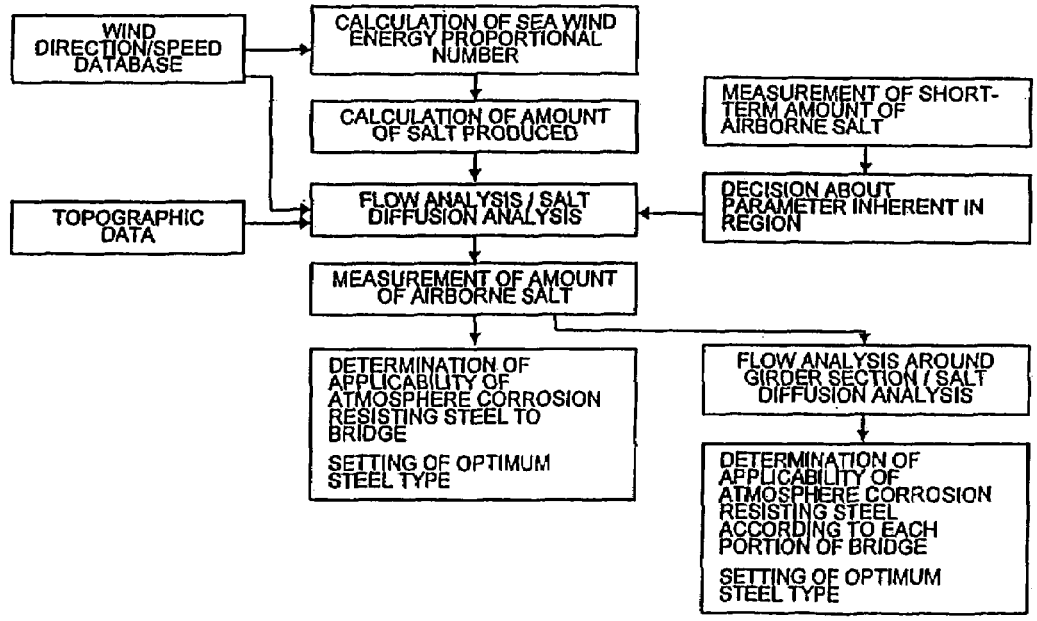
FIG. 2 is a flowchart showing another example of the conventional method for determining the applicability of the atmospheric corrosion resistant steel.
Figure 3:
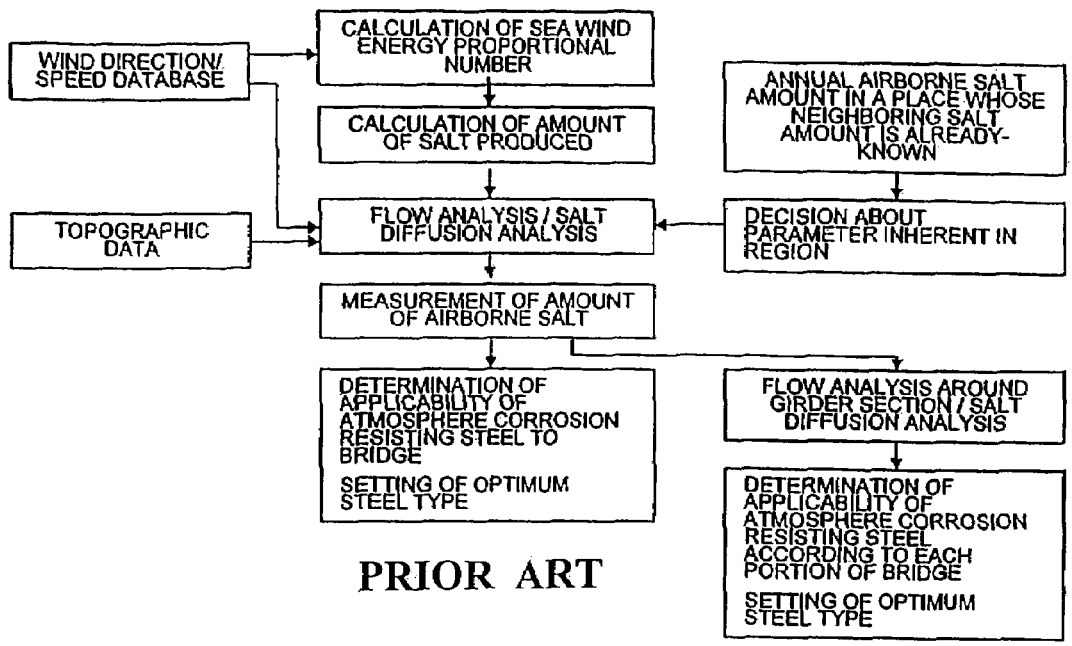
FIG. 3 is a flowchart showing still another example of the conventional method for determining the applicability of the atmospheric corrosion resistant steel.
Figure 4:
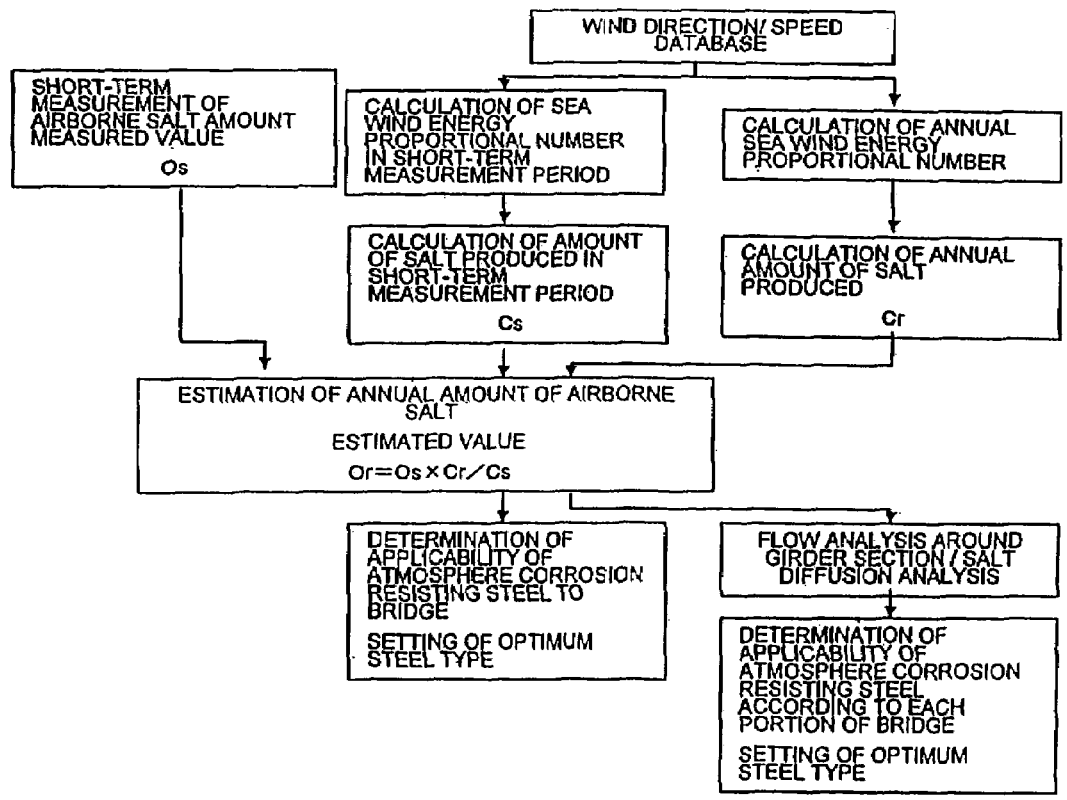
FIG. 4 is a flowchart showing yet another example of the conventional method for determining the applicability of the atmospheric corrosion resistant steel.
Figure 5:
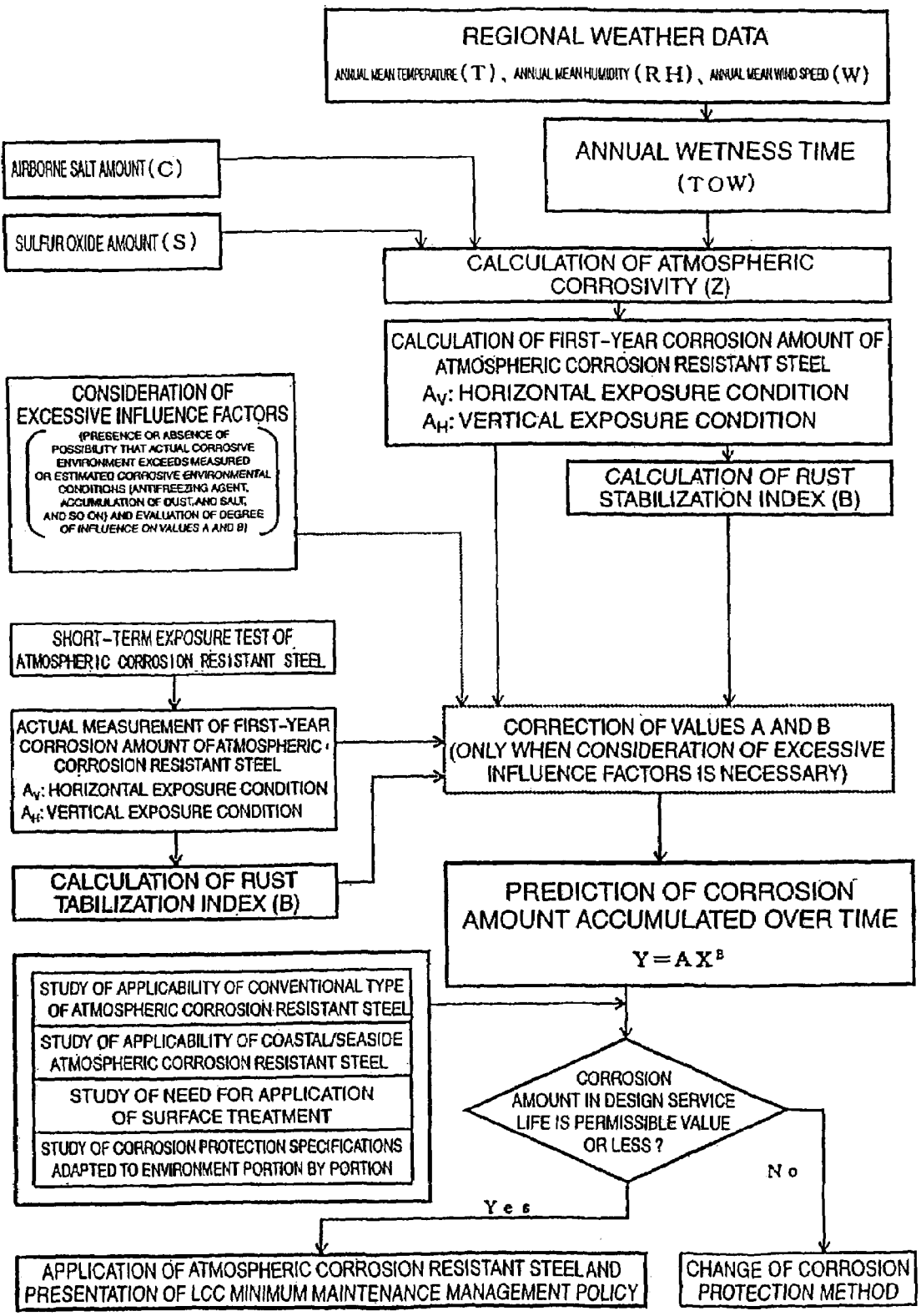
FIG. 5 is a flowchart showing a method for predicting the amount of corrosion and a method for judging the applicability of an atmospheric corrosion resistant steel based on an exemplary embodiment of a method according to the present invention.
Figure 29:
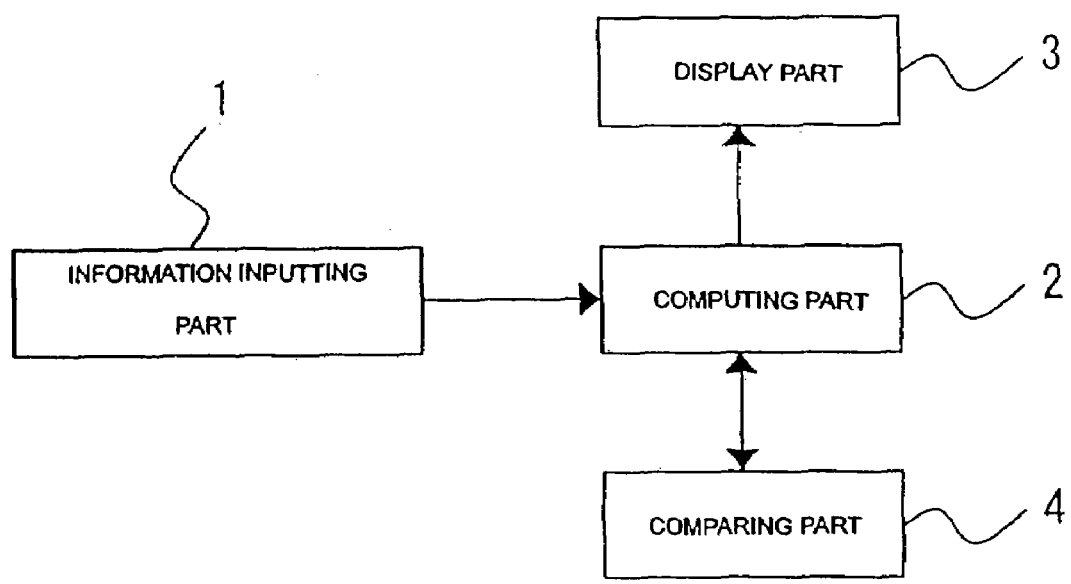
FIG. 29 is a block diagram showing an example of a processing system capable of performing exemplary steps shown in FIG. 5.

FIG. 5 illustrates a flowchart for an exemplary embodiment of a method according to an embodiment of the present invention for predicting an amount of corrosion and a method for judging the applicability of an atmospheric corrosion resistant steel. FIG. 29 shows a block diagram of an exemplary embodiment of a processing system according to the present invention which is capable of performing steps shown in FIG. 5.

In the processing system shown in FIG. 29, information, for example, on the amount of airborne salt, the amount of sulfur oxide, and regional weather data in FIG. 5 is inputted to a computing part 2 via an information inputting part (input means) 1. The information inputting part 1 may be a keyboard for a personal computer or the like, or an interface board for an electrical communication line or the like. The computing part (computing means) 2 performs a computation such as the calculation of a first-year corrosion amount, calculation of a rust stabilization index, correction of a value A and a value B, and prediction of a corrosion amount accumulated over time. A display part (display unit) 3 displays, for example, information outputted from the computing part 2. Note that not only the display part 3 but also a printer, for example, may be provided as an output means. A comparing part 4 compares a corrosion amount and a permissible value for judging whether a corrosion amount in a design life period in FIG. 5 is the permissible value or less.

Figure 6:
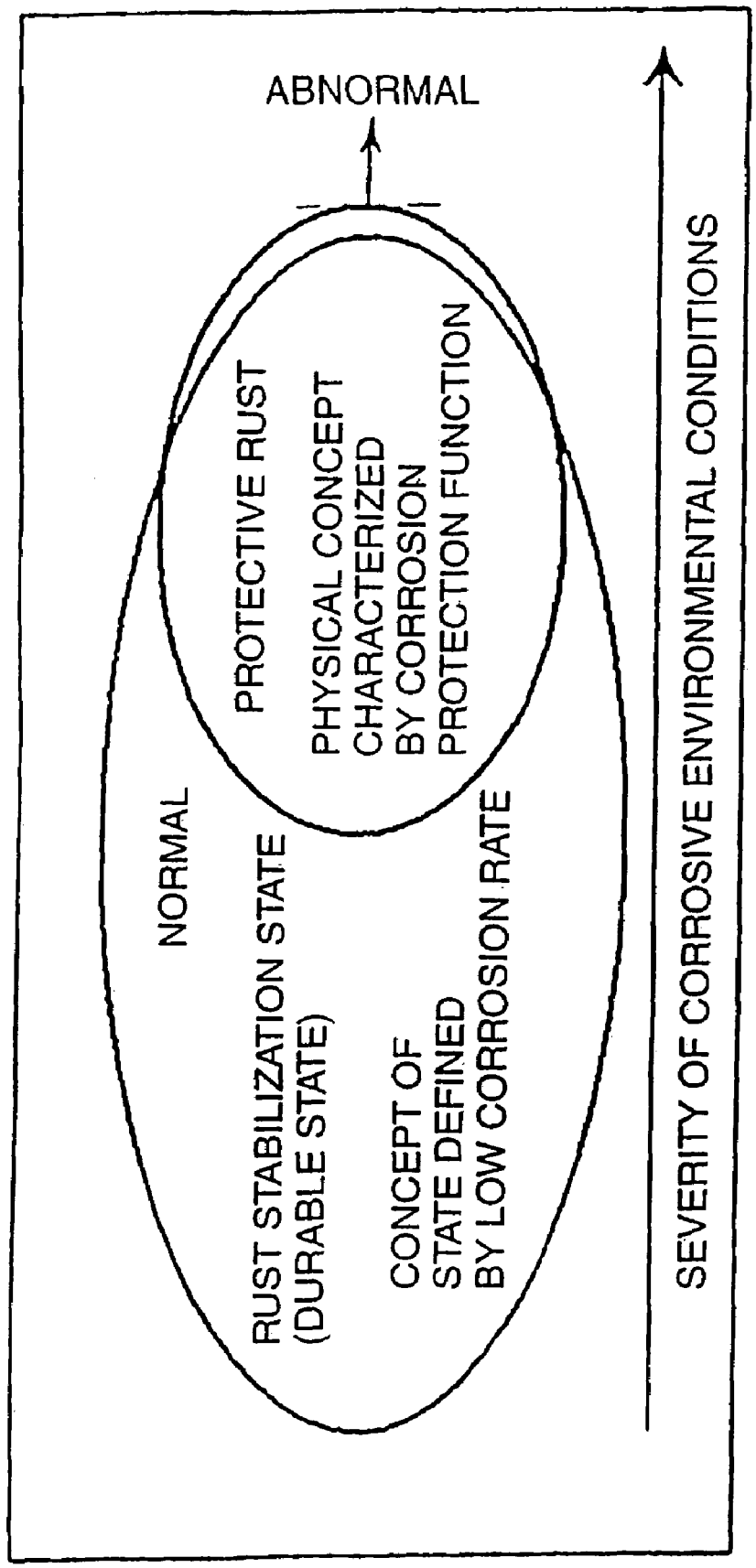
FIG. 6 is a diagram illustrating a concept of a rust stabilization state.

FIG. 6 shows an exemplary concept which may be used as a background of the aforementioned definition (proposal) of rust stabilization. As shown in FIG. 6, the corrosion itself does not progress if environmental conditions are sufficiently mild, whereby the protective function of rust is hardly enhanced, but the load carrying capacity of the structure becomes stable over a long period of time. If the environmental conditions become severe, protective rust may be formed by the effect of alloy components, and thanks to its corrosion inhibiting effect, the load carrying capacity of the structure becomes stable over a long period of time. Either of the aforementioned states can be regarded as "a normal state" for the atmospheric corrosion resistant steel from the viewpoint of load carrying capacity. Accordingly, this state can be represented by "a rust stabilization state". On the other hand, if the environmental conditions become severer, the corrosion inhibiting effect reaches its limit even if the protective rust is temporarily formed, sometimes leading to "an abnormal state" for the atmospheric corrosion resistant steel such as the occurrence of accelerated corrosion. A limit point at which the normal state cannot be maintained any longer is called a rust stabilization limit condition.

An analysis using the basic concept of the corrosion phenomenon of the atmospheric corrosion resistant steel can be pursued based on FIG. 6 in fundamental principal. First, when the atmospheric corrosion resistant steel is exposed to an environment within the rust stabilization limit condition, in which the atmospheric corrosion resistant steel is subjected to repetition of moderate dryness/wetness, a secular reduction in corrosion rate occurs according to the formation of protective rust. In order to model this situation, if the number of years elapsed is taken as X, a corrosion rate $V_x$ after X year(s) can be represented by an equation (Eq. 1) with a corrosion rate $V_1$ and an index β when the number of years elapsed is one. According to this equation (Eq. 1), the corrosion rate when X=0 is infinite, but since this corrosion rate is a theoretical corrosion rate on the assumption that this state is a state in which the steel is totally uncoated, that is, a state in which the steel is not coated even with a passive film, for example, immediately after the steel has been subjected to shot blast, this is insignificant from an engineering viewpoint.

$$v_x = v_1 \cdot \frac{1}{X^\beta} \tag{Eq. 1}$$

If both sides of the equation (Eq. 1) are integrated with respect to X, an accumulated corrosion amount Y after X years can be found, and an equation (Eq. 2) may be obtained.

$$Y = \int_{x=0}^{x} v_x dX = \frac{v_1}{1-\beta} X^{1-\beta} \tag{Eq. 2}$$

In this manner, if the amount of first-year corrosion (first-year corrosion amount) is taken as A as an initial condition, the value of A is represented by an equation (Eq. 3).

$$A = Y_{(x=1(year))} = \int_{x=0}^{1} v_x dX = \frac{v_1}{1-\beta} \tag{Eq. 3}$$

Moreover, by letting 1−B
β=B and calling the value of B as a stabilization index, a prediction formula of the corrosion amount accumulated over time of the atmospheric corrosion resistant steel which is empirically well-known can be obtained by substituting the equation (Eq. 3) in the equation (Eq. 2).

$$Y = AX^B \tag{Eq. 4}$$

Figure 7:
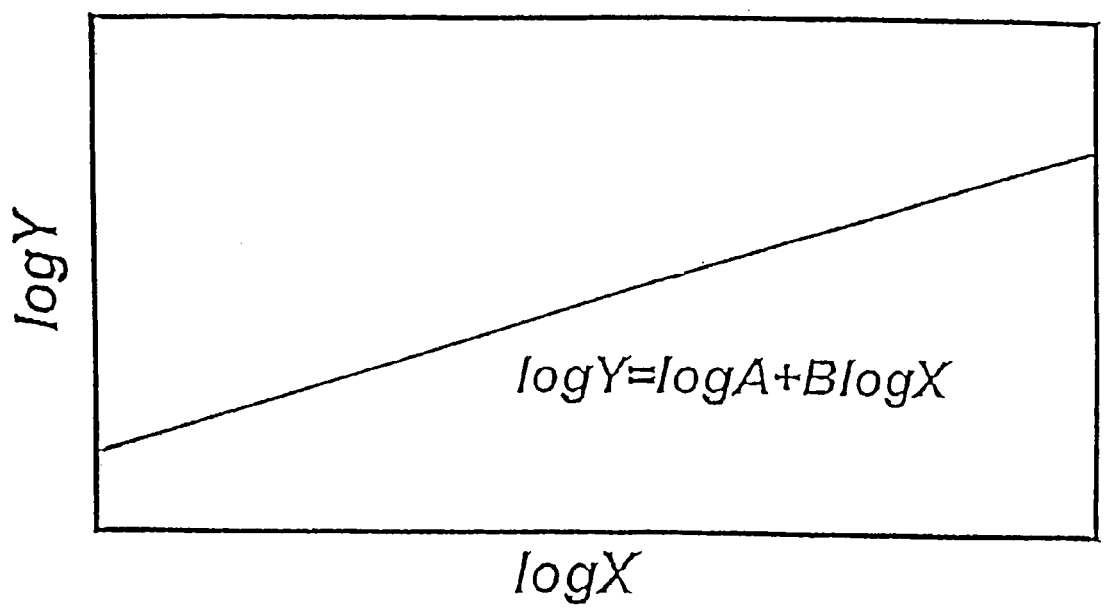
FIG. 7 is a diagram schematically showing a relation between a corrosion amount accumulated over time Y and the number of years elapsed X based on Eq. (4) with two logarithmic axes.

FIG. 7 shows the relation of logarithms on both sides of the equation (Eq. 4). As shown in FIG. 7, there is a linear relationship between logX and logY, and to predict Y accurately, it is indispensable to estimate the first-year corrosion amount A and the rust stabilization index B with sufficient precision. In particular, as for the atmospheric corrosion resistant steel, when long-term usage is taken into consideration, the value of the rust stabilization index B with linear inclination taken according to the stabilization of rust formed on the surface is an important factor.

Further, the result of the study of the equation (Eq. 4) in relation to FIG. 6 is as follows. When the severity of a corrosive environment is low, the rust stabilization index B takes a value almost close to one, and corrosion progresses almost in accordance with a linear rule. However, since the first-year corrosion amount A is extremely small, the corrosion rate is very slow, leading to the realization of the rust stabilization state in which the secular deterioration of load carrying capacity of the structure is insignificant from an engineering viewpoint.

As the severity of the corrosive environment becomes higher gradually, the first-year corrosion amount A becomes larger, but the rust stabilization index B becomes smaller since the formation of protective rust is promoted. As a result, the rust stabilization state thanks to a secular reduction in corrosion rate can be realized. When the severity of the corrosive environment further increases, the protectiveness of rust is lost, thereby both the first-year corrosion amount A and the rust stabilization index B increase, and consequently abnormal corrosion occurs in a severe corrosive environment beyond the rust stabilization limit condition.

When it is thought that the corrosion rate in a state in which the protectiveness of rust is low is determined by the environmental conditions and the corrosion resistance of a steel material, the first-year corrosion amount A can be approximately expressed by functions of an equation (Eq. 5).

$$A = F(Z) \cdot G(w) \tag{Eq. 5}$$

where Z is an atmospheric corrosivity index, w is a corrosion resistance index of the steel material, F(Z) and G(w) are functions representing the contribution of the corrosivity index Z and the corrosion resistance index w to the first-year corrosion amount A. If components of the steel material are determined, the corrosion resistance index G(w) is fixed, whereby it becomes a subject of discussion how the corrosivity index Z is found and then related to the first-year corrosion amount A.

The environmental conditions are generally considered to be complex including many factor changes. Until now, the environmental conditions under which the atmospheric corrosion resistant steel is used is first approximately set by the amount of airborne salt, but even under an environment with an airborne salt amount beyond 0.05 mdd, the atmospheric corrosion resistant steel sometimes is in a good rust stabilization state. Hence, there is an objection to the way in which its applicability condition is determined only by a single index. On the other hand, there is an example in which the correlation between various pieces of weather data and the corrosion rate is statistically analyzed, but a sufficient conclusion is not necessarily obtained. One of reasons for this is that no study is made in terms of chemical kinetics.

Hence, the corrosivity of an atmospheric environment is studied on the basis of the aforementioned arguments. A hypothetical way of thinking for deriving a corrosivity index of the atmospheric environment performed on trial this time will be explained systematically.

(i) The corrosivity of the atmospheric environment is proportional to an annual wetness time TOW (h).

(ii) In a region where an annual mean wind speed W (m/sec.) is high, the wetness time TOW (h) is short because of a drying effect.

(iii) As an airborne salt amount C (mdd) increases, the corrosivity of the atmospheric environment increases.

(iv) As a sulfur oxide amount S (mdd) increases, the corrosivity of the atmosphere increases, but the influence of the sulfur oxide amount is smaller than that of the airborne salt amount.

(v) When the sulfur oxide amount S (mdd) increases in a region where the airborne salt amount C (mdd) is large, the corrosion inhibiting effect thanks to sulfur oxide is produced. It is thought that this is because sulfate ions are adsorbed into rust, negatively charged rust is formed, and thereby the invasion of chloride ions is prevented.

(vi) Concerning the influence of an annual mean temperature T (K), the relation of Arrhenius, which is the basics of chemical kinetics, holds.

(vii) Assuming that in an inside girder (under a bridge girder), the atmospheric corrosion resistant steel is exposed, the rain's effect of cleaning adherents is not expected.

When the atmospheric corrosivity index Z with respect to the atmospheric corrosion resistant steel exposed under the bridge girder is formulated based on the aforementioned way of thinking, an equation (Eq. 6) is obtained.

$$Z = \alpha \cdot TOW \cdot \exp(-\kappa \cdot W) \cdot \frac{C + \delta \cdot S}{1 + \varepsilon \cdot C \cdot S} \cdot \exp\left(\frac{-E_a}{R \cdot T}\right) \quad \text{(Eq. 6)}$$

where $\alpha$ is a coefficient to make the value of the index Z within a numerical region of an order which is easy to handle and can be determined artificially. $\kappa$, $\delta$, and $\varepsilon$ are constants respectively representing the degree of influence of each of factors which they are associated with. R(J/K·mol)) is a gas constant. $E_a$ is activation energy of a corrosion reaction, and if reference is made to the conventional research results, for example, $5 \times 10^3$ J/mol may be substituted as a representing value.

The value of each of the influence degree constants $\kappa$, $\delta$, and $\varepsilon$ is found, for example, in the following manner. First, the first-year corrosion amount A, the airborne salt amount C, and the sulfur oxide amount S of an SMA-type atmospheric corrosion resistant steel obtained in the results of exposure tests of 41 bridges all over the country regarding the atmospheric corrosion resistant steel conducted by the following three: Public Works Research Institute of the Ministry of Construction; Japan Association of Steel Bridge Construction; and the Kozai Club, and stipulated by JIS G 3114 are found. Additionally, the annual mean temperature T, an annual mean humidity RH, and the annual mean wind speed W in the neighborhood of each of places where the exposure tests are executed are found from weather data in 1999 which is measured and disclosed by each weather station. Moreover, the annual wetness time TOW is found from the annual mean temperature T and the annual mean humidity RH by a method by Kucera et al. (V. Kucera, J. Tidblad, A. A. Mikhailov: ISO/TC156/WG4-N314 Annex A, Mar. 30, 1990, the entire disclosure of which is incorporated herein by reference). Then, natural environmental conditions at each exposure test place are calculated as the atmospheric corrosivity index Z by the equation (Eq. 6), and the influence degree constants $\kappa$, $\delta$, and $\varepsilon$ are determined in the following manner so as to obtain the best correlation with the first-year corrosion amount A. More specifically, initial values of the influence degree constants $\kappa$, $\delta$, and $\varepsilon$ which are regarded as appropriate in terms of chemical kinetics are inputted, and while the values of these three constants are systematically changed, an optimum solution of a combination of the influence degree constants $\kappa$, $\delta$, and $\varepsilon$ which minimizes a deviation in the correlation between the first-year corrosion amount A and the atmospheric corrosivity index Z is found numerically and analytically. The optimum values may be, for example, $\kappa=0.1$, $\delta=0.05$, and $\varepsilon=60$.

The degree of influence on the first-year corrosion amount of the atmospheric corrosion resistant steel of various kinds of weather factors which have been hitherto considered to be unclarified natural phenomena can be mathematically modeled as the corrosivity index Z for the first time.

Figure 8:
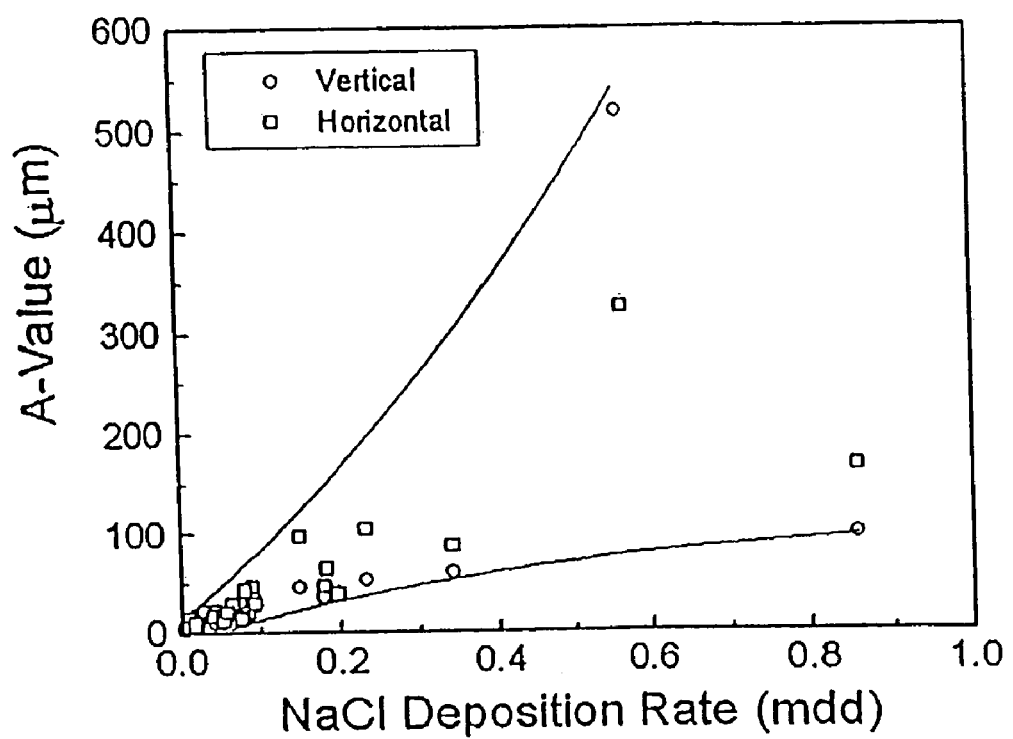
FIG. 8 is a diagram showing a relation between an airborne salt amount C and a first-year corrosion amount A.

Based on the aforementioned data, the relation between the airborne salt amount C and the first-year corrosion amount A obtained by a method hitherto performed is shown in FIG. 8. Moreover, the relation between the corrosivity index Z calculated based on the equation (Eq. 6) and the first-year corrosion amount A is shown in FIG. 9 and FIG. 10 while being classified into a vertical exposure member and a horizontal exposure member.

Figure 9:
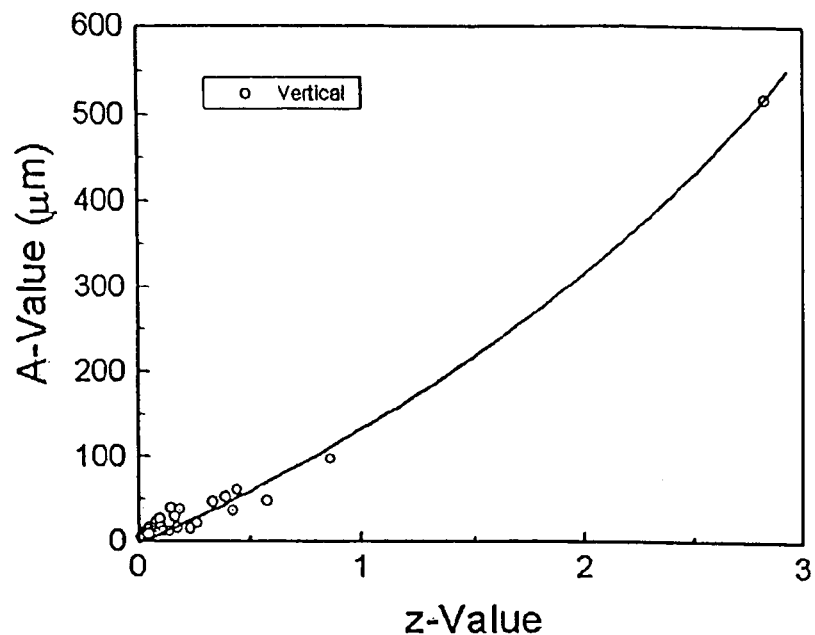
FIG. 9 is a diagram showing the relation between a corrosivity index Z and the first-year corrosion amount A of a vertical exposure member.
Figure 10:
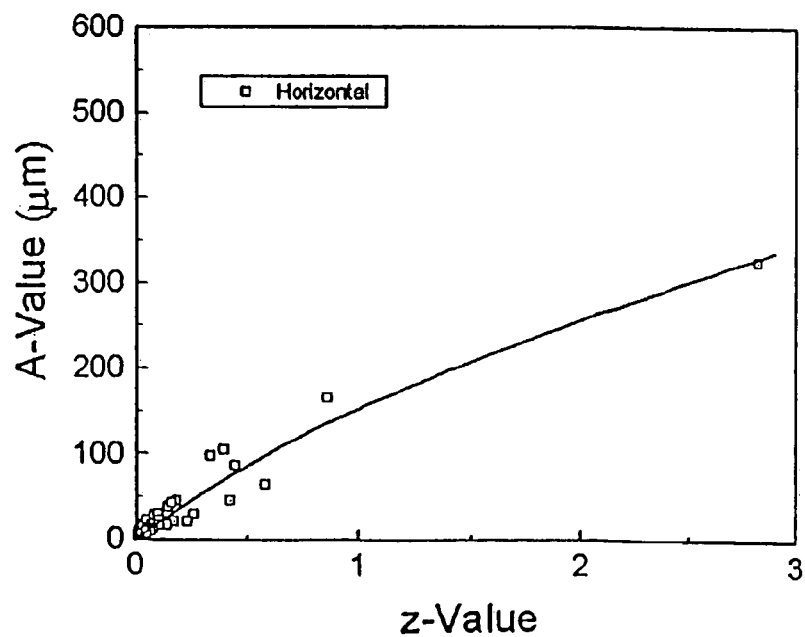
FIG. 10 is a diagram showing a relation between the corrosivity index Z and the first-year corrosion amount A of a horizontal exposure member.

From a comparison between the graphs of FIG. 8 and FIG. 9 and a comparison between the graphs of FIG. 8 and FIG. 10, it can be ascertained that the first-year corrosion amount A can be estimated with a far smaller error by a method of the present invention in which the value of the first-year corrosion amount A is found with the corrosivity index Z than a conventional method in which the severity of corrosive environment is represented by the airborne salt amount C only.

A horizontal specimen and a vertical specimen are different in a situation in which corrosive substances adhere to the surface thereof, whereby a difference in corrosion rate occurs inevitably. Thus, when a quadric regression analysis is performed with a first-year corrosion amount Av of the vertical exposure member and a first-year corrosion amount $A_H$ of the horizontal exposure member with respect to the corrosivity index Z shown in FIG. 9 and FIG. 10, equations, (Eq. 7a) and (Eq. 7b), are obtained. This means that the aforementioned F(Z) function can be found. Moreover, curves shown in FIG. 9 and FIG. 10 are curves represented by the equations, (Eq. 7a) and (Eq. 7b), respectively.

$$A_v(\mu m) = 37.60Z^2 + 74.44Z + 7.37 \ (p = 7.64 \times 10^{-39}) \quad \text{(Eq. 7a)}$$

$$A_H(\mu m) = -24.16Z^2 + 182.19Z + 4.05 \ (p = 1.12 \times 10^{-23}) \quad \text{(Eq. 7b)}$$

When, in this description, the numerical values regarding only the vertical exposure member and only the horizontal exposure member, or numerical values regarding data obtained from only the vertical exposure member and only the horizontal member are described distinctively, the description is given distinctively with symbols such as "$A_V$" and "$A_H$" corresponding to verticality (V) and horizontally (H). On the other hand, when verticality and horizontally are mixed or distinction is unnecessary since verticality and horizontally are equal, the description is given with no distinction with symbols such as "A" and so on.

In each of the equation (Eq. 7a) and the equation (Eq. 7b), the value of p used for a determination of significance of regression analysis is shown in parentheses. When the value of p is larger than 0.05, this relational expression is determined to be rejected by the null hypothesis. However, since the value of p in each equation is extremely small, these regression analyses can be determined to be sufficiently significant statistically.

The first-year corrosion amount A found in each of the aforementioned equation (Eq. 7a) and equation (Eq. 7b) is a mean value, and hence it is insufficient to show a prediction range. A weather data observation site and a bridge construction site have different environmental conditions, whereby the occurrence of variations is inevitable. Hence, semilogarithmic plots in FIG. 9 and FIG. 10 are made to evaluate the range of the variations, and prediction results are presented in the form of a range with an upper value as 1.7 times as many as the mean value and a lower value as 1/1.7 times as many as the mean value, as shown in an equation (Eq. 8aU), an equation (Eq. 8aL), an equation (Eq. 8bU), and an equation (Eq. 8bL).

$$A_V^{Upper} = 1.7 A_V \quad \text{(Eq. 8aU)}$$

$$A_V^{Lower} = \frac{1}{1.7} A_V \quad \text{(Eq. 8aL)}$$

$$A_H^{Upper} = 1.7 A_H \quad \text{(Eq. 8bU)}$$

-continued $$A_H^{Lower} = \frac{1}{1.7}A_H \quad \text{(Eq. 8bL)}$$

The corrosivity index Z represents macro corrosivity of the atmospheric environment, whereas, in terms of the way of thinking, the values of the first-year corrosion amount $A_H$ of the horizontal exposure member and the first-year corrosion amount $A_V$ of the vertical exposure member are values corresponding to atmospheric corrosivity to the atmospheric corrosion resistant steels placed under a horizontal exposure condition and a vertical exposure condition, respectively. Returning to FIG. 6 again and advancing the study in this sense allows a prediction that some relationship is obtained if a plot is made with the first-year corrosion amount A as the horizontal axis and the rust stabilization index B as the vertical axis.

Figure 11:
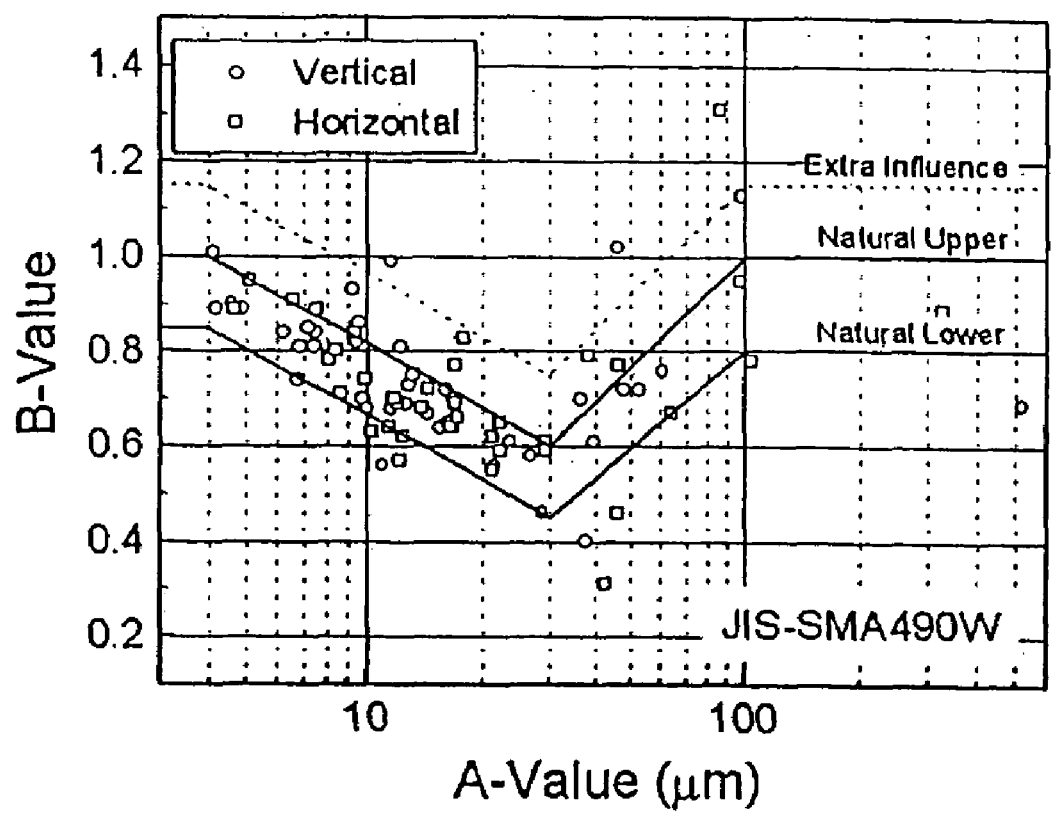
FIG. 11 is a diagram showing a relation between the first-year corrosion amount A and a stabilization index B and its interpretation.

Hence, if the aforementioned results of exposure tests of 41 bridges all over the country are plotted in this manner, a graph shown in FIG. 11 is obtained. From FIG. 11, the following tendency is perceived although there are variations. Namely, within the range of the first-year corrosion amount A up to about 30 μm, the rust stabilization index B reduces, whereby the long-term effect of reducing the corrosion rate can be expected. On the other hand, in the severe corrosive environment in which the first-year corrosion amount exceeds about 30 μm, the rust stabilization index B increases, whereby there is a tendency for abnormal corrosion to easily occur. Such a tendency is newly found out. It should be noted that FIG. 11 represents a basic concept in FIG. 6 for the first time by quantitative data.

In the estimation of the rust stabilization index B, the inventor et al. of the present application seek related theories in which variations are smaller while referring to weather data and the like, but they cannot obtain a better correlation than that in FIG. 11. Hence, a method for predicting the rust stabilization index B is laid down with the thought that FIG. 11 can be interpreted as follows.

(i) Variations in data can be interpreted as having occurred since corrosive factors such as the spraying of an antifreezing agent, deposition of dust or salt, which cannot be grasped by the measurement of corrosive environment exist, whereby a reduction in the rust stabilization index B is hindered. Hereinafter, such corrosive factors are called excessive influence factors.

(ii) When the extent to which the excessive influence factors inhibit rust stabilization is extremely low, the rust stabilization index B is within a band in which 80% or more of measurement points are distributed. Hereinafter, this state is called a natural state.

(iii) In the natural state, the probability that the rust stabilization index B exceeds a Natural Upper line is low.

(iv) In the natural state, the probability that the rust stabilization index B is lower than a Natural Lower line is low.

(v) When the excessive influence factors which cannot be grasped in the initial environmental measurement act, it seems appropriate that a normal upper standard approximately at the level of influence in Japan is estimated to be a level shown by an Extra Influence line, but it is also suitable to review and input again the measurement results of the environmental conditions and make a prediction calculation again under the condition of the natural state. The level shown by the Extra Influence line is an excessive influence value of the rust stabilization index B and represented by a natural upper value of the rust stabilization index B plus 0.15. Hereinafter, the excessive influence value of the rust stabilization index B is called an excessive influence B value, and the natural upper value of the rust stabilization index B is called a natural upper B value. Similarly, a natural lower value of the rust stabilization index B is called a natural lower B value, an excessive influence value of the first-year corrosion amount A is called an excessive influence A value, and a natural upper value of the first-year corrosion amount A is called a natural upper A value.

According to the aforementioned interpretation, it is possible to represent the range of the rust stabilization index B in the natural state estimated by using environmental data with the natural upper B value and the natural lower B value. The excessive influence A value is presumed to be approximately the natural upper A value, and thereby the value obtained by multiplying the natural upper A value by 1.0 is adopted as a normal standard. Moreover, the natural upper B value plus 0.15 is adopted as a normal standard of the rust stabilization index B in the excessive influence state. However, the degree of excessive influence may change according to the circumstances, whereby it is necessary to make a study while adjusting its value on the basis of the natural upper A value and the natural upper B value. It should be understood that calculation by an excessive influence mode is a simple method only for indicating the standard as described above.

Since the value of A is a value corresponding to the first-year corrosion amount, it is possible from the above description to estimate the value of A based on weather data, the amount of airborne salt, and the amount of sulfur oxide. It is also possible to find the value of A by an actual exposure test.

By setting the aforementioned distribution band of the first-year corrosion amount A and the rust stabilization index B, the result of the prediction calculation is also displayed in the form of a band. When the statistical analysis of the amount of corrosion after 100 years is carried out based on a result of statistically analyzing a prediction range with the environmental conditions and a result predicted from actual measurement data, it turns out that except for several cases where remarkable excessive influence exists, a natural upper line and a natural lower line of a predicted corrosion/wear curve coincide with about 98% and 2% of a cumulative normal distribution curve, respectively. Hence, by adding a realization probability to the predicted corrosion curve, the interpretation of a calculation result can be examined with higher accuracy.

Recently, new high-performance atmospheric corrosion resistant steels called coastal/seaside atmospheric corrosion resistant steels are developed and introduced on the market by domestic steel manufacturers. Among them, only a coastal atmospheric corrosion resistant steel of Nippon Steel Corporation has long-term exposure data on conditions under a bridge girder. However, the number of pieces of data is smaller as compared with that of a JIS type atmospheric corrosion resistant steel (hereinafter, steel materials stipulated by JIS G 3114 and JIS G 3125 are collectively called a JIS type atmospheric corrosion resistant steel), and it is difficult to grasp and analyze the correlation with the aforementioned systematic weather data. However, at the present time when the influence of airborne salt on the seashore or caused by the spraying of an antifreezing agent is pointed out, it is desirable to present a predicted value of the corrosion amount accumulated over time as a standard in order to minimize the occurrence of defects of new steel materials due to excessive expectation and safely realize LCC minimization. Therefore, a predicting method for a 3Ni-0.4Cu based coastal atmospheric corrosion resistant steel is laid down on a basis of the aforementioned method for predicting the corrosion amount accumulated over time of the JIS type atmospheric corrosion resistant steel in the following way of thinking.

The corrosion amount accumulated over time of the coastal atmospheric corrosion resistant steel is subjected to an expression represented by $Y=AX^B$.

The coastal atmospheric corrosion resistant steel is a steel material having lower corrosion and dissolution activity, whereby the first-year corrosion amount A of the coastal atmospheric corrosion resistant steel is smaller than that of the JIS type atmospheric corrosion resistant steel.

The coastal atmospheric corrosion resistant steel is a steel in which a reduction in pH at a corrosion interface is inhibited by the formation of Ni-containing rust (Zairyo-to-Kankyo, vol. 49, No. 1, pages 30–40 (2000), the entire disclosure of which is incorporated herein by reference), and therefore the level of the rust stabilization index B of the coastal atmospheric corrosion resistant steel is lower than that of the JIS type atmospheric corrosion resistant steel.

When, based on the aforementioned way of thinking, the first-year corrosion amount A and the rust stabilization index B of the 3Ni-0.4Cu based coastal atmospheric corrosion resistant steel and the JIS type atmospheric corrosion resistant steel (JIS-SMA490W;JIS G 3114) as a comparative example are found from the result of an exposure test under a bridge girder in which they are subjected to horizontal exposure for nine years at the quay in Kimitsu City where the amount of airborne salt is 1.3 mdd, the result in Table 1 can be obtained. Here, the 3Ni-0.4Cu based coastal atmospheric corrosion resistant steel is a steel material, for example, disclosed in Japanese Patent Application No. 2-125839, Japanese Patent Application No.11-172370, and "Zairyo-to-Kankyo, vol. 49, No. 1, pages 30–40 (2000)", the entire disclosure of which are incorporated herein by reference.

TABLE 1

| parameter | 3Ni-0.4Cu Steel | JIS-SMA490W | Ratio |
| --- | --- | --- | --- |
| A(μm) | 120 | 220 | 0.55 |
| B | 0.72 | 0.95 | 0.76 |

From the result shown in Table 1, the first-year corrosion amount A of the 3Ni-0.4Cu based coastal atmospheric corrosion resistant steel is a value obtained by multiplying the first-year corrosion amount A of the JIS-SMA atmospheric corrosion resistant steel by 0.55, and the level of the rust stabilization index B of the 3Ni-0.4Cu based coastal atmospheric corrosion resistant steel is a value obtained by multiplying the level of the rust stabilization index B of the JIS-SMA atmospheric corrosion resistant steel by 0.76. Hence, based on this relation, the prediction of the corrosion amount accumulated over time as a standard is made. Incidentally, the result in Table 1 is the result of long-term exposure under such excessive influence conditions that, though it is exposure under a bridge girder, the scale is far smaller than that of an actual bridge, the dew condensation time is long, and that a large amount of salt and dust is deposited. In a condition under an actual bride girder under which a good breeze is got and less deposits are collected than under the aforementioned condition, the absolute values of both the first-year corrosion amount A and the rust stabilization index B are thought to be smaller. The ratio of the first-year corrosion amount A and the ratio of the rust stabilization index B between the JIS type atmospheric corrosion resistant steel and the 3Ni-0.4Cu based atmospheric corrosion resistant steel cancel the aforementioned problem of absolute values due to the exposure condition, and hence they are thought to be effective. Incidentally, also as concerns the method for predicting the corrosion/wear of the 3Ni-0.4Cu based atmospheric corrosion resistant steel, the concrete method has been described here, but respective coefficients of other steel materials can be also found by accumulating future data. It is possible to predict the corrosion/wear of these new steel materials in the same manner, and it is needless to say that this case is also within the scope of the present invention.

According to the definition (proposal) of rust stabilization, in order to further enhance the function by the surface treatment, it is far more advantageous to select a method for forming protective rust slowly and surely than to accelerate corrosion to shorten the period of the formation of the protective rust. In other words, it is effective to maintain the load carrying capacity of a structure over a very long period of time without repainting by the substitution for the protective rust eventually while reducing the corrosion rate of the steel material as low as possible, and as a result of the manifestation of this function, the occurrence of outflow rust can be also prevented. From a result of an exposure test over a period of 20 years to 30 years for the atmospheric corrosion resistant steel commercialized from long ago to which a phosphoric acid based PVB based surface treatment method is applied and application results of steel structures, it is proved that this concept can be realized.

The effect of the surface treatment for forming the protective rust slowly and surely can be provisionally estimated as a standard by the following way of thinking.

(i) In the atmospheric corrosion resistant steel subjected to the surface treatment for forming the protective rust slowly and surely, corrosion and wear are completely prevented until a step of deterioration of an organic coating is completed.

(ii) At the time when the step of deterioration of the organic coating of the surface treatment for forming the protective rust slowly and surely is completed, the protective film is formed on the surface of the atmospheric corrosion resistant steel by the effect of a protective film formation promoter contained in a primer.

(iii) As a result, the corrosion rate of the atmospheric corrosion resistant steel at a point in time when the deterioration of the organic coating has been completed is lower than that of the bare atmospheric corrosion resistant steel at an early stage.

Information about the number of years the corrosion and wear of the atmospheric corrosion resistant steel have been completely prevented is necessary to estimate the effect of the surface treatment applied to a region under study based on the aforementioned qualitative hypothesis. Regarding this information, setting seems to change variously according to specifications of the surface treatment. With reference to remarks based on actual results of steel materials manufacturers and surface treatment manufacturers, the number of years is inputted to software, so that the effect can be provisionally estimated. Incidentally, the on-set time is determined during the deterioration period of the organic coating, and at the same time, in view of the aforementioned effect, the corrosion/wear curve is moved in parallel in the direction of an exposure period axis by the period of deterioration of the organic coating of the atmospheric corrosion resistant steel subjected to the surface treatment, so that the prediction of the corrosion amount with the influence of the surface treatment taken into consideration becomes possible.

Moreover, by multiplying the predictively calculated first-year corrosion amount A and rust stabilization index B of the bare atmospheric corrosion resistant steel by a surface treatment effect coefficient with respect to the first-year corrosion amount A and the rust stabilization index B found from exposure data on the atmospheric corrosion resistant steel subjected to the surface treatment, the corrosion/wear curve of the surface treatment atmospheric corrosion resistant steel can be calculated. Thereby, also as concerns the first-year corrosion amount A and the rust stabilization index B, the prediction of the corrosion amount with the influence of the surface treatment taken into consideration can be realized.

When importance is attached to a landscape or when its application to a region with severe corrosive environment is planned, surface treatment or repainting is sometimes performed not only at an early stage but also every several decades. Such a calculating method as enables the prediction of the long-term corrosion/wear amount in the aforementioned design which is predicated on repainting is premised on a concept that the corrosion rate is zero while a surface treatment film or a painting film presents no problem, and the corrosion rate presents a proper corrosion rate in a state in which the surface treatment film or the painting film is deteriorated.

According to an exemplary embodiment of the present invention, the minimum maintenance very long-term durability design of atmospheric corrosion resistant steel structures which can contribute to an improvement in the financial standing of the nation or a local government can be made with facility by a user who does not necessarily have a detailed knowledge of the complicated corrosion phenomenon of the atmospheric corrosion resistant steel. As a result, the provision of safe, secure, and low life-cycle cost infrastructure is furthered. Hence, potentiality which leads to the regeneration of industrial competitiveness of the entire nation increases. Prediction technology of the present invention, which is a new idea using a natural phenomenon of the corrosion of the atmospheric corrosion resistant steel, can be improved to raise its precision with the further progress of the study. However, it is needless to say that even in this case, its basic portion is in the category of the present invention. When the results of calculation by the thus established method for predicting the long-term corrosion loss of the atmospheric corrosion resistant steel was compared with hitherto accumulated actual exposure test data, it could be confirmed that these two coincided well. It could be verified that the predicting method of the present invention is appropriate.

It may need enormous labor and time to deal with calculation procedures one by one when the aforementioned new way of thinking and the invention based thereon are executed. Hence, in order that everybody can easily predict the long-term corrosion/wear amount of the atmospheric corrosion resistant steel with a personal computer, the effective and efficient manifestation of the aforementioned significance is tried by developing calculatable software with VISUAL BASIC (registered trademark) 6.0 of MICROSOFT (registered trademark) Corporation as a language.

Software according to one of exemplary embodiment of the present application can be used to implement the method(s) according to the present invention using the system according to the present invention.

Figure 12:
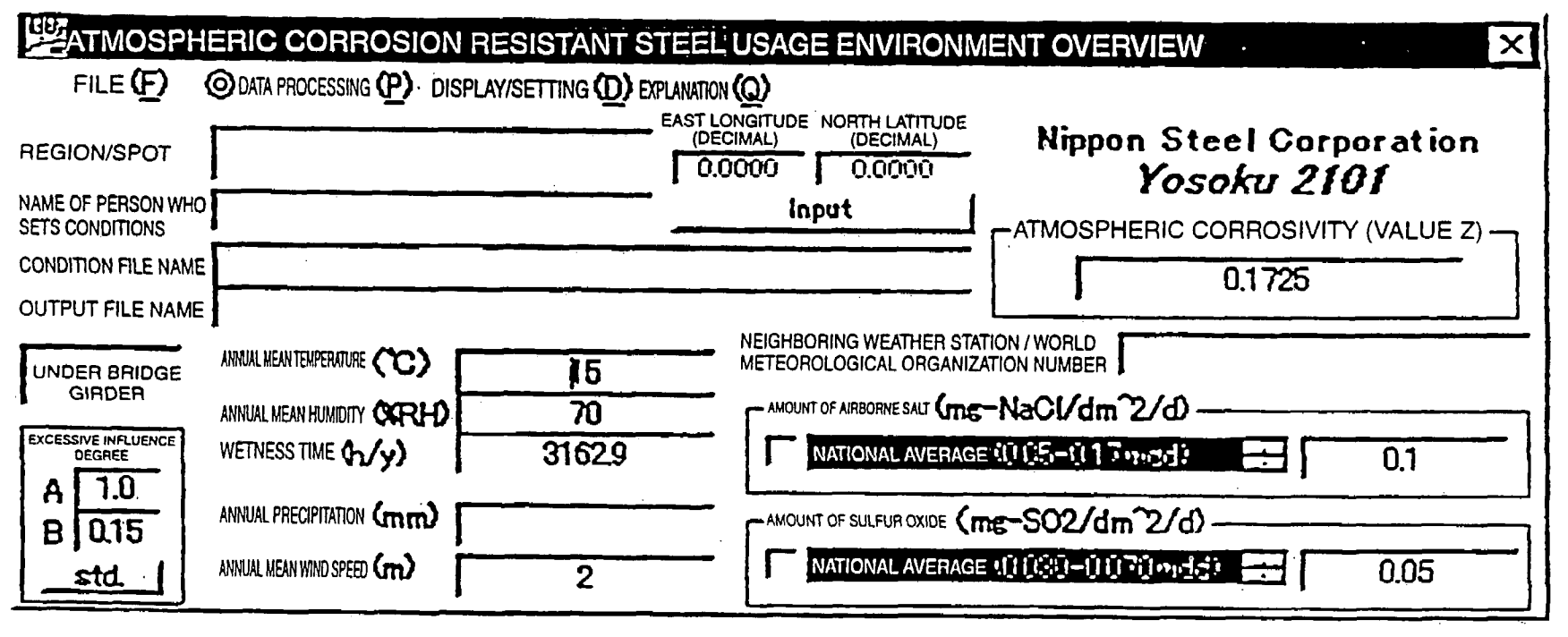

First, in a panel (screen) of "Atmospheric corrosion resistant steel Usage Environment Overview" shown in FIG. 12, environmental conditions are set. In an environmental condition setting screen, weather data and airborne salt/sulfur oxide data of a desired region are inputted, a region/spot name and its neighboring meteorological observatory information are inputted, and a condition file (.YSK) is created and stored by a menu operation. Moreover, the storage place and name of an output file (.CSV) to which the prediction result is outputted are set.

It should be mentioned that the wetness time TOW and the atmospheric corrosivity index Z are automatically calculated from input data. Moreover, the annual precipitation is not used in the calculation of this software, but it is desirable to input and store it as a reference value. As for the airborne salt amount and the sulfur oxide amount, if their measurement values can be obtained, the values are inputted. When their measurement values cannot be obtained, it is possible to click a checkbox and set an approximate value from five levels in Japan as an assumed value. When the prediction result is used for the design of an actual structure or the like, it is thought that the condition setting including a judgment about whether or not to use this software is accompanied by its appropriate accountability. Therefore, the name of a person who sets the conditions is entered. When the corrosion amount for one year is known by actual exposure, the prediction calculation based on the actually measured first-year corrosion amount A can be performed by inputting the first-year corrosion amount A by the menu operation of this screen and switching mode setting.

The values of longitude and latitude of a construction side are represented by decimal conversion of fractions smaller than a degree. For display or input in degree, minute, and second, an "Input" button is clicked to display a panel shown in FIG. 13. A selection between east longitude and west longitude, a selection between north latitude and south latitude, and an input of the values of the degree, minute, and second are made, and then if a "=" button is clicked, the value obtained by the decimal conversion of fractions smaller than the degree is calculated and displayed. Further, when a "result transfer" button is clicked, an input operation of data on latitude and longitude is completed.

Figure 14:
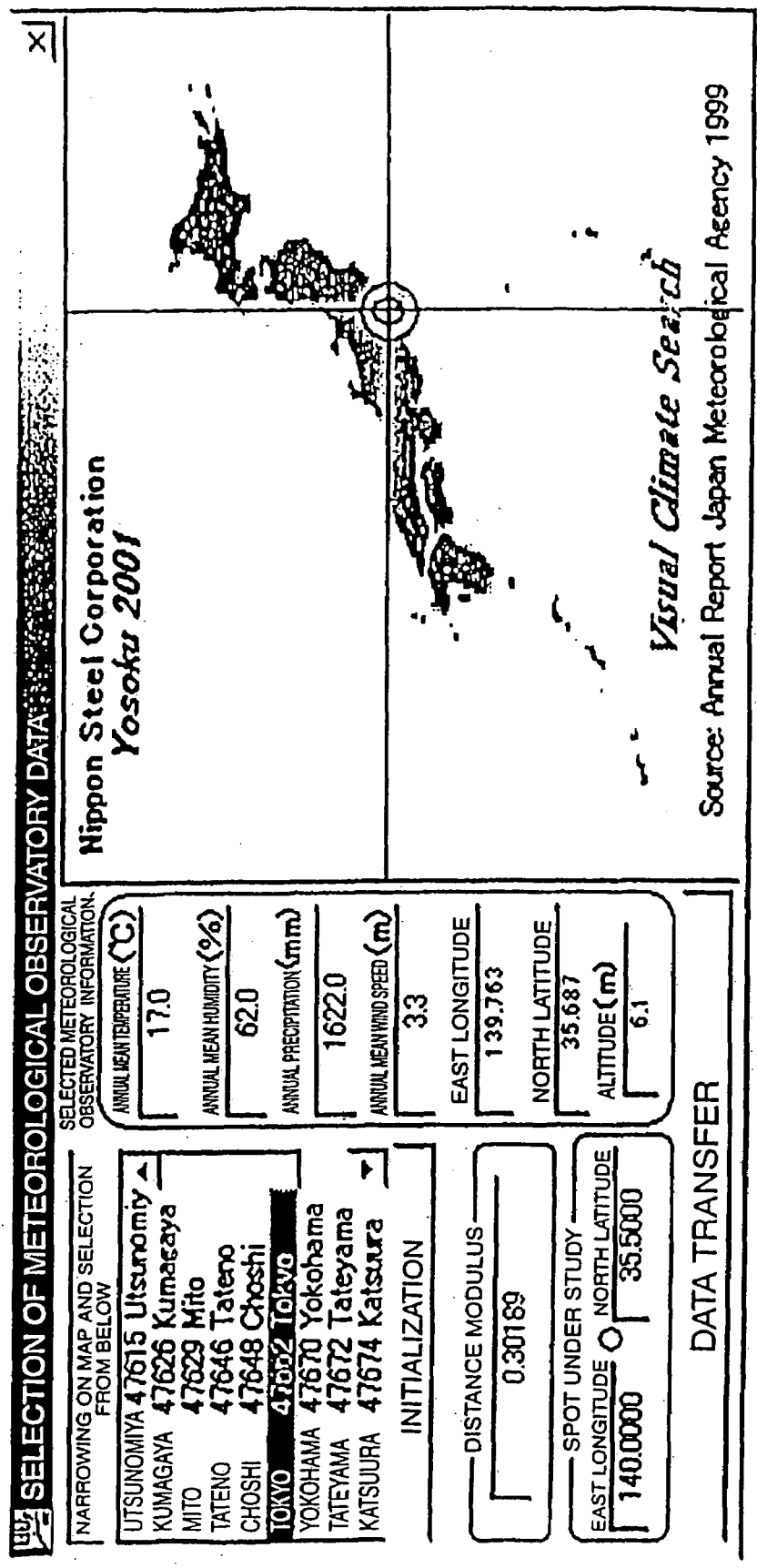
FIG. 14 is a chart showing an example of a panel for obtaining weather data of the long-term corrosion/wear prediction software for the atmospheric corrosion resistant steel.

The weather data can be also set easily. Setting values can be easily inputted from a database to a text box shown in the screen of the aforementioned "Atmospheric corrosion resistant steel Usage Environment Overview" by clicking data processing and "Visual Climate Search (not shown)" by the menu operation to activate a panel shown in FIG. 14. On this occasion, if the latitude and longitude of a spot under study are inputted in advance, a database selection operation becomes more efficient. A small red circle is shown at a point corresponding to the latitude and longitude inputted in advance on a map of the Visual Climate Search. A range is displayed by a mouse operation within the map, and meteorological observatories can be narrowed down to those within the range. If meteorological observatories in the vicinity of the read circle mark are extracted and thereafter one is selected from a list box, its latitude and longitude are shown on the map, and the distance modulus is calculated and displayed. The smaller the distance modulus, the smaller differences in latitude and longitude are.

The distance modulus indicates differences in latitude and longitude in a plane, and thereby referring to the altitude of the weather observation site, the selection operation is advanced. When a "data transfer" button is clicked, selected weather conditions are automatically inputted to the screen of the "Atmospheric corrosion resistant steel Usage Environment Overview". Note that this panel is devised so that weather data within Japan can be easily inputted, and the setting of weather conditions necessary for calculation can be also inputted manually. Namely, the prediction of long-term corrosion/wear of the atmospheric corrosion resistant steel in overseas countries is possible, and the effect of the present invention is not limited within Japan, and in fact can be utilized throughout the world.

Figure 15:
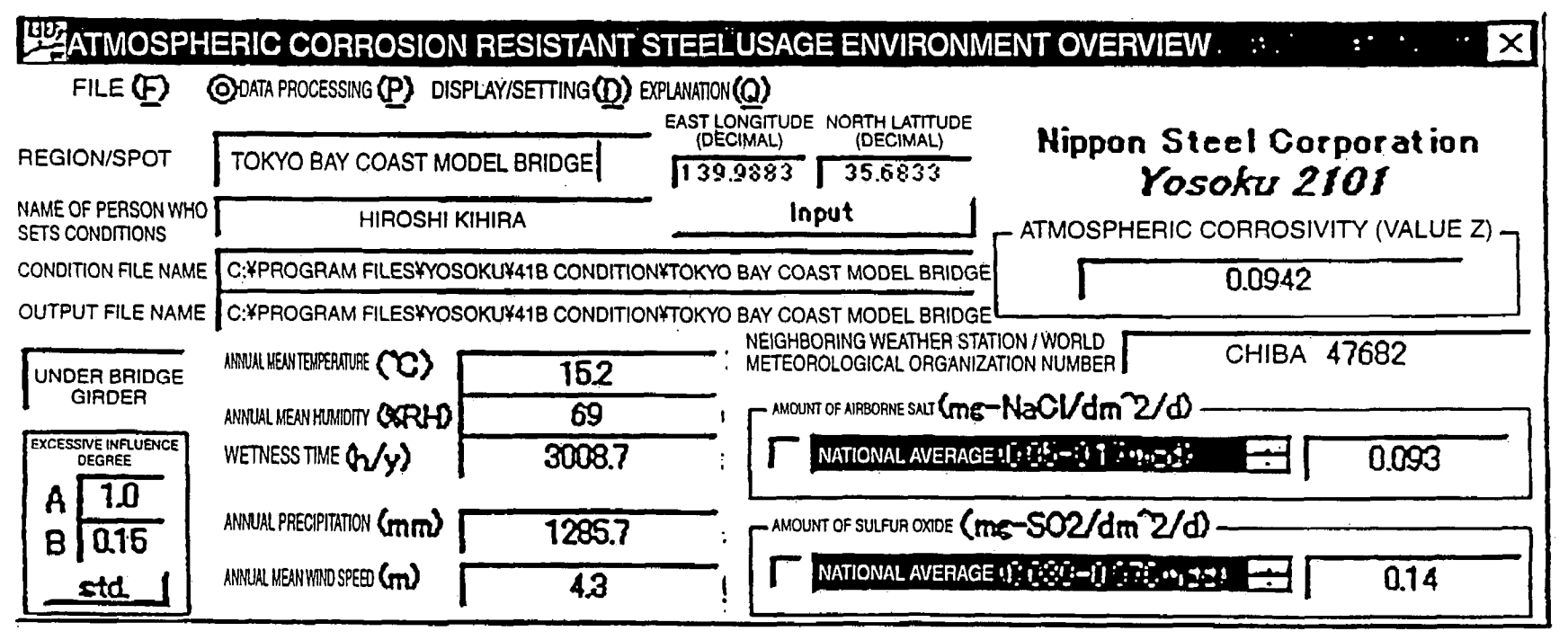

Before executing calculation, the excessive influence degree is confirmed by a panel shown in FIG. 15. General values of a scaling factor with respect to the natural upper A value and a value added to the natural upper B value are shown by default. In a case where very strong excessive influence is predicted or the like, these values should be set a little larger in some cases. The predicting method with the excessive influence degree which was not included in the environmental measurement value taken into account seems to be unnecessary since a prediction calculation in a natural state based on proper measurement results needs to be originally made, but when the environment seems to be severer than the early stages of construction in maintaining and managing the actual bridge, it is thought that it is a convenient function to display an empirical standard value. Therefore, the function of changing the excessive influence degree is added to this software. After all the condition setting input is completed, the "data processing" is selected by the menu operation, and then "Execute Calculation of Value A and Value B" is selected to move to a screen of "Parameter Calculation results". Then, "to Secular Prediction" is selected by the menu operation, and by clicking "Execute Calculation", a panel of "Secular Corrosion Prediction Overview" is displayed.

In the panel of Parameter Calculation Results (Assumption of Bridge Inside Girder) shown in FIG. 16, the estimated results of the first-year corrosion amount A and the rust stabilization index B can be seen. The corrosion and wear of the atmospheric corrosion resistant steel are predicted by an expression represented by $Y=AX^B$ (Y: one-sided corrosion amount accumulated over time, X: number of years elapsed) which is generally accepted. In the panel of "Parameter Calculation Results", estimated values of the first-year corrosion amount A and the rust stabilization index B based on the setting conditions are displayed. The prediction range in a state in which the extent to which the rust stabilization is inhibited by excessive influence factors such as the influence of spraying of the antifreezing agent, deposition of salt, and retention of condensation water is very low is displayed with a natural lower value (cumulative normal value 2% value) and a natural upper value (cumulative normal probability 98% value). The standard value when the extent to which the rust stabilization is inhibited by the excessive influence factors is large is displayed at the same time. A shift to a panel of "Calculation Results Overview Reference" is made by the menu operation or clicking a button of "Next".

Based on constant prediction values displayed in the previous panel, 2%, 50%, and 98% probability values of the one-sided corrosion/wear prediction values of each condition of the atmospheric corrosion resistant steel (SMA) and the coastal atmospheric corrosion resistant steel (3Ni-0.4Cu) after 10 years, 50 years, and 100 years, under the horizontal or vertical exposure condition are calculated. The results of this calculation can be seen in a panel shown in FIG. 17.

Figure 18:
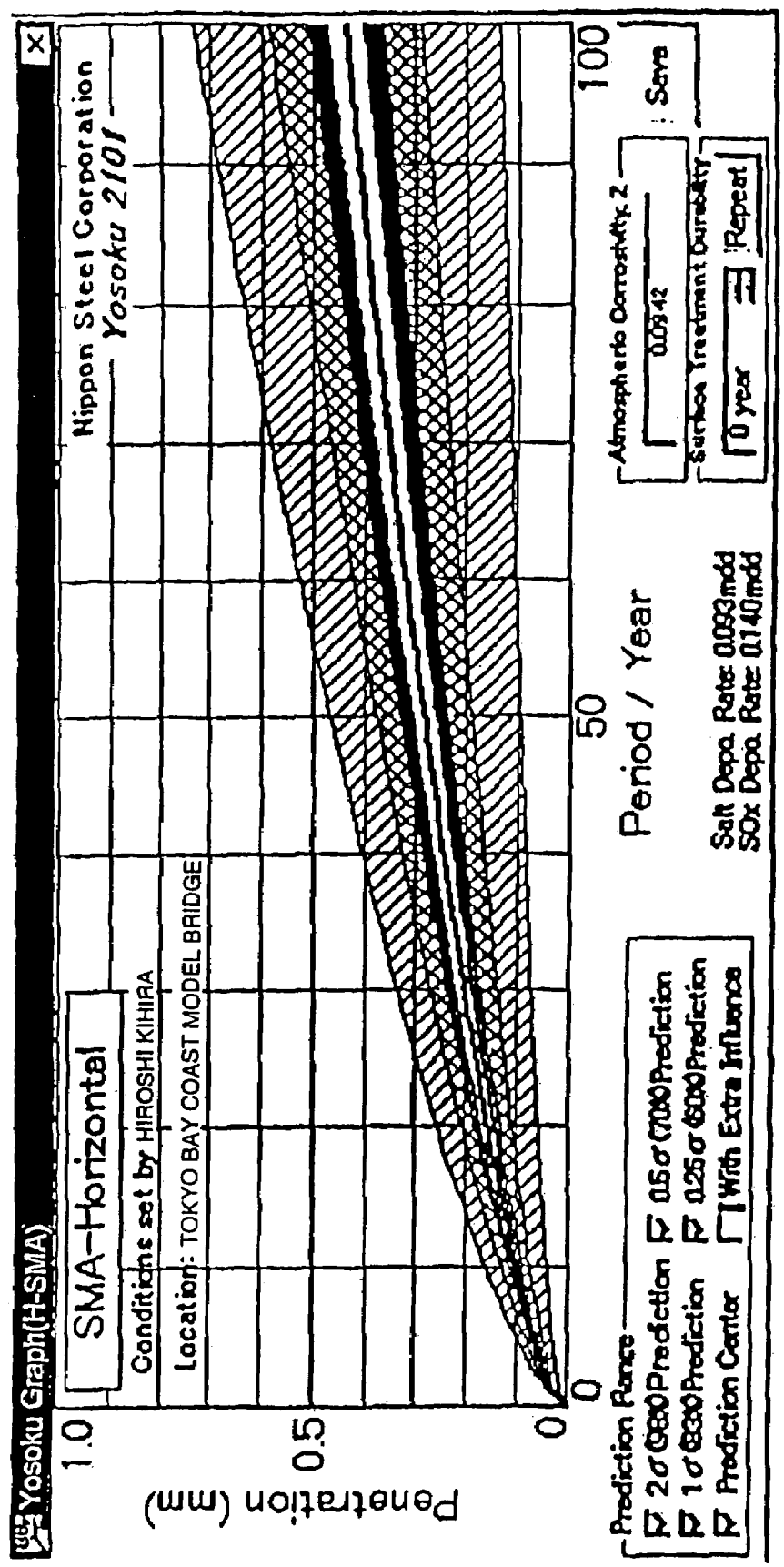
FIG. 18 is a chart showing an example of a panel for viewing calculation results of long-term corrosion/wear prediction when a bare JIS type atmospheric corrosion resistant steel is used.

When a button at the lower end of the panel of "Secular corrosion Amount Prediction Overview" is clicked, a corrosion curve predicted by the calculation can be displayed in graphical form as shown in FIG. 18. A hatched region in the graph is a predicted region of corrosion and wear (range of 2σ) in the natural state, and this range is further divided into regions of 1σ, 0.5σ, and 0.25σ, which are displayed. Namely, it is possible to add the realization probability to the predicted corrosion/wear curve and display (represent) it. Also in the following FIG. 19, FIG. 20, FIG. 21, FIG. 22, FIG. 24, FIG. 26, and FIG. 27, it is possible to add the realization probability to the predicted corrosion/wear curve and display (represent) it. Display/non-display of a desired probability region can be reset by operating a checkbox at the lower left. According to arguments in recent academic conferences, concerning both concrete and steel, design and maintenance management need to be performed on the assumption that corrosion and deterioration occur on a long-term basis. Moreover, as for structures to be constructed, there is such a movement that a plan of maintenance management ought to be formed from the stage of designing.

Figure 19:
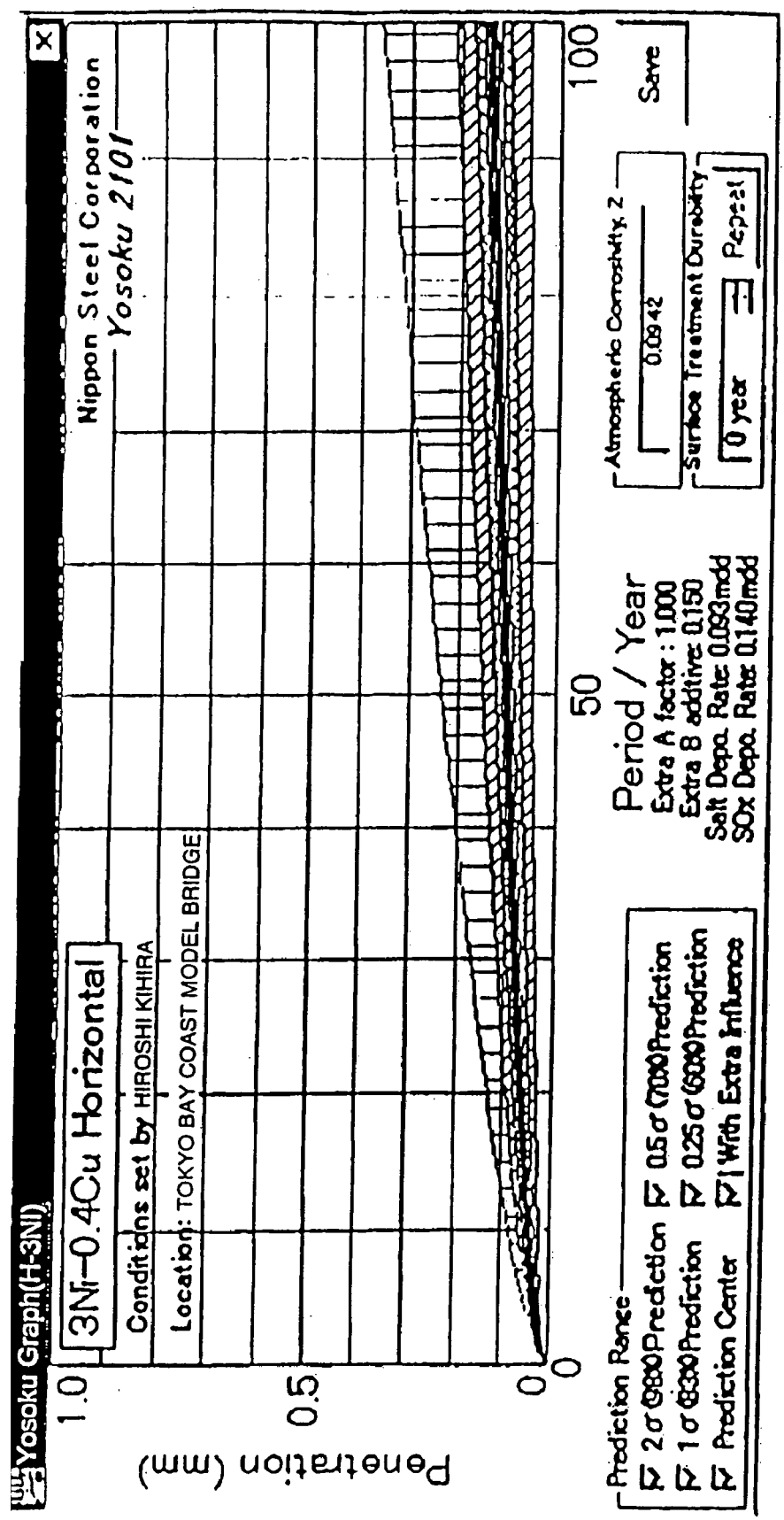
FIG. 19 is a chart showing an example of a panel graphically displaying calculation result of long-term corrosion/wear prediction of a coastal atmospheric corrosion resistant steel with excessive influence taken into consideration.

Based on the calculation results of this software, application policies of steel materials and a surface treatment method, the design of bridges, and maintenance management policies are required to be studied so that the corrosion amount can be limited to within approximately 0.3 mm on one side in 50 years and 0.5 mm on one side in 100 years, this corrosion amount hardly affecting the load carrying capacity and usability of steel bridges. In the calculation example in FIG. 18, it is determined that when a bare horizontal member of the JIS type atmospheric corrosion resistant steel (SMA-Horizontal) is used under these environmental conditions, there is a possibility of exceeding a corrosion amount of 0.5 mm in 100 years at a probability of about 30%. Hence, a prediction calculation is made with 3Ni-0.4Cu based costal atmospheric corrosion resistant steel as a steel material, the result exemplified in FIG. 19 is obtained. Incidentally, a calculated value with excessive influence taken into consideration is also shown by a vertically hatched region. From this result, if the steel material is the 3Ni-0.4Cu based coastal atmospheric corrosion resistant steel, minimum maintenance is judged to be sufficiently possible in the use of the bare atmospheric corrosion resistant steel under these environmental conditions.

Figure 20:
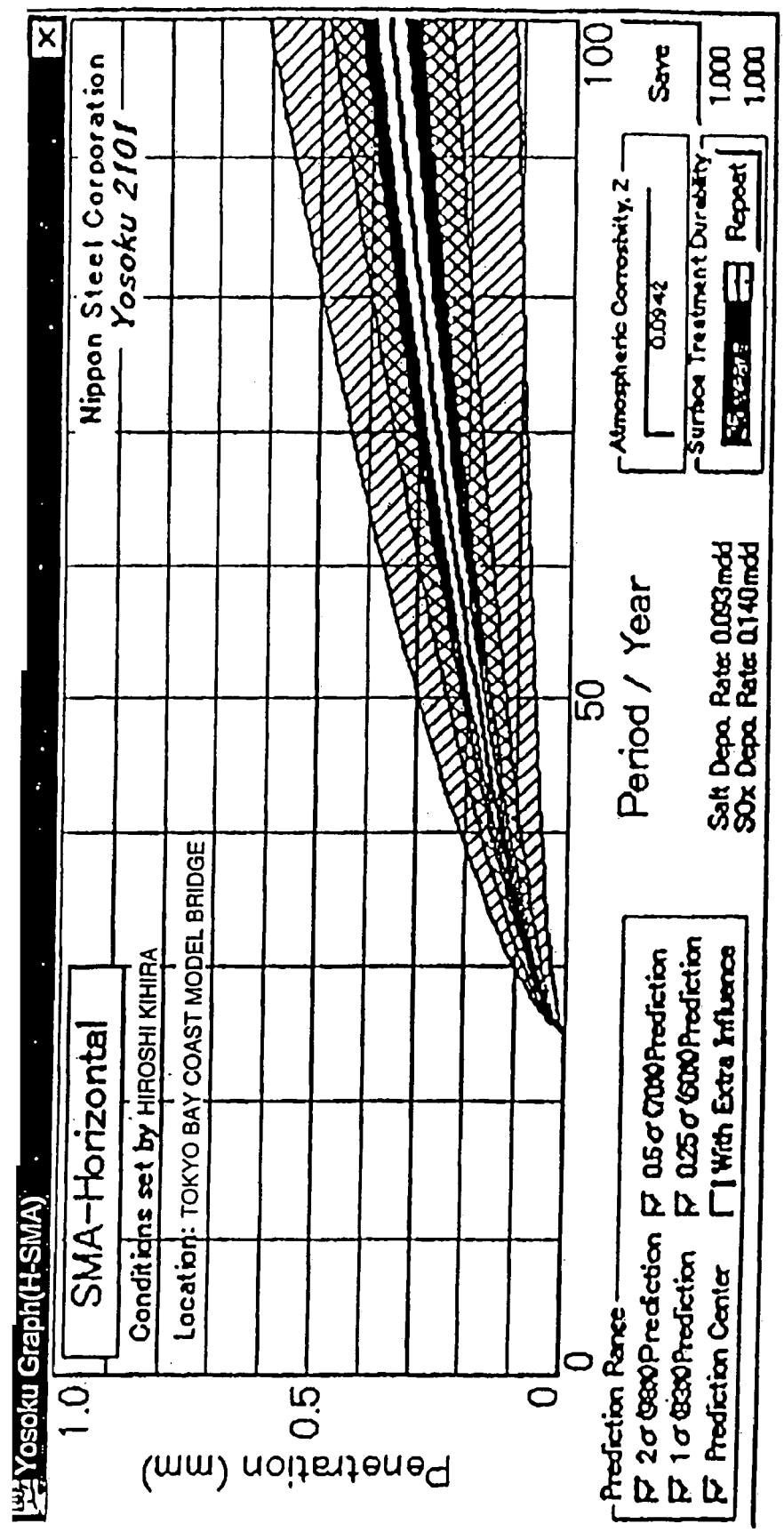
FIG. 20 is a chart showing an example of a panel graphically displaying calculation results of long-term corrosion/wear prediction when the JIS type atmospheric corrosion resistant steel is subjected to general surface treatment.
Figure 21:
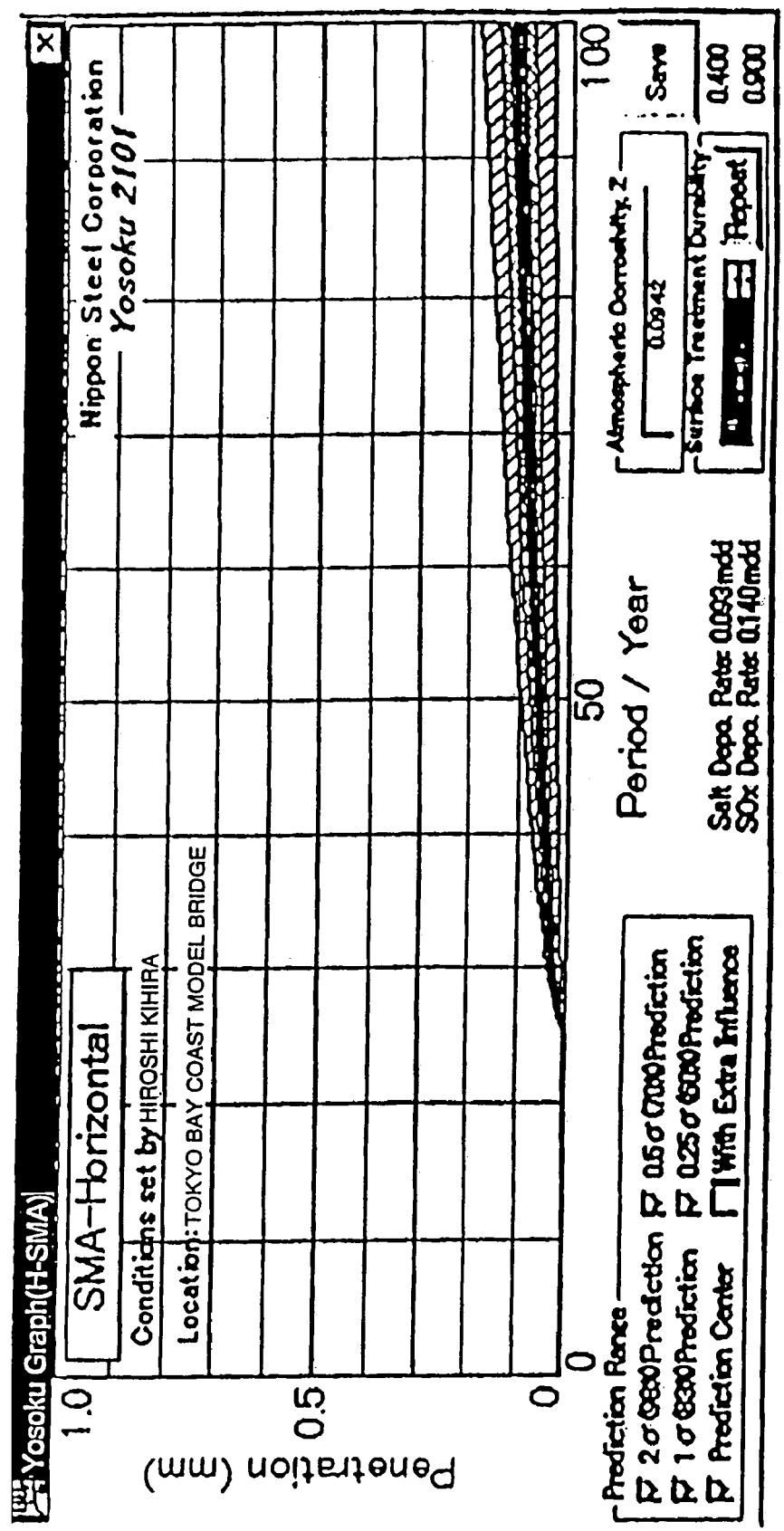
FIG. 21 is a chart showing an example of a panel graphically displaying calculation results of long-term corrosion/wear prediction when the JIS type atmospheric corrosion resistant steel is subjected to surface treatment for the atmospheric corrosion resistant steel.
Figure 22:
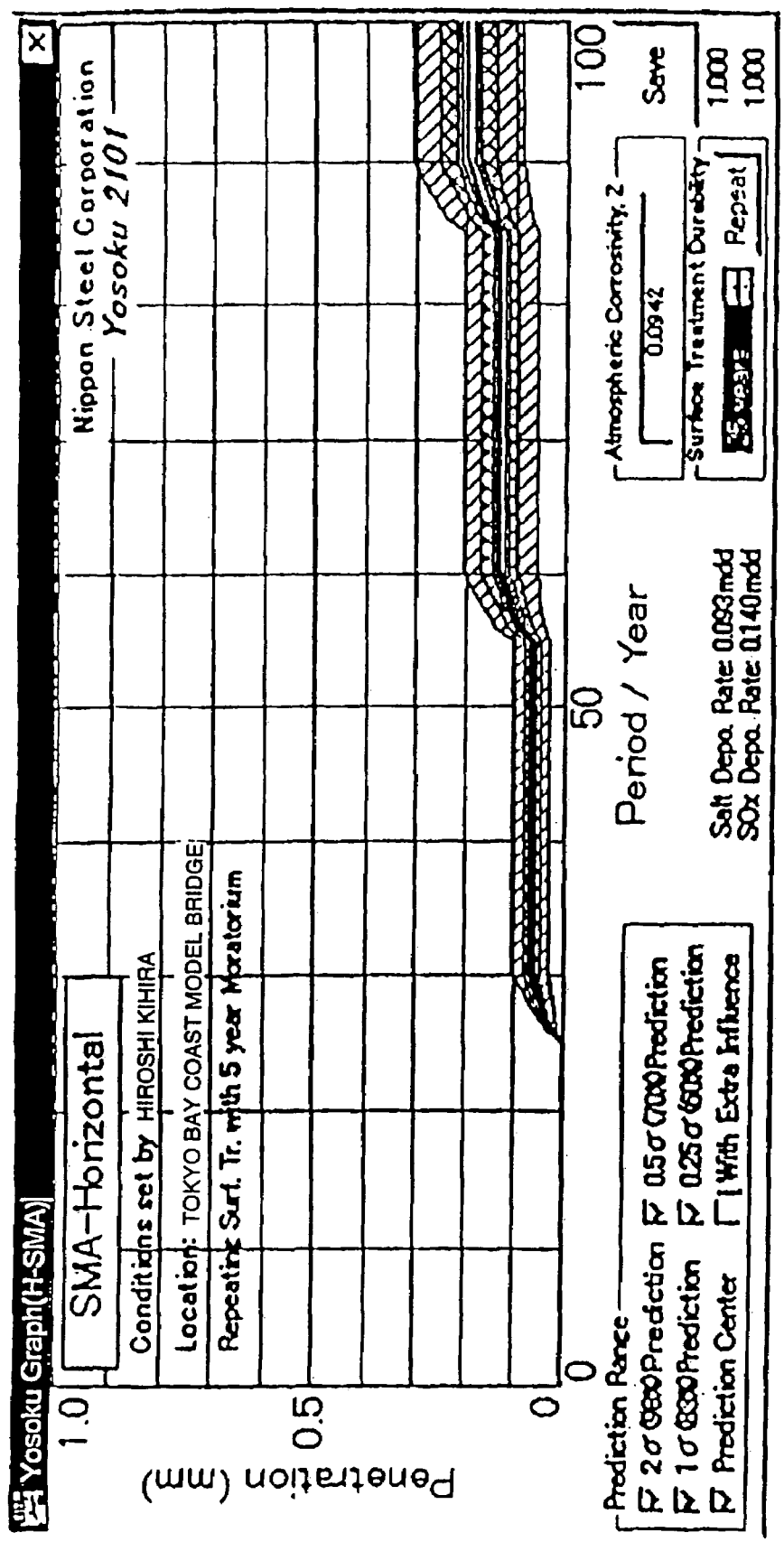
FIG. 22 is a chart showing an example of a panel graphically displaying calculation result of long-term corrosion/wear prediction by a method of repainting the JIS type atmospheric corrosion resistant steel by the general surface treatment.

For the purpose of further inhibiting the corrosion of the atmospheric corrosion resistant steel and the coastal atmospheric corrosion resistant steel, a surface treatment method which promotes rust stabilization slowly and surely is sometimes used, whereby a list box is set up at the lower right of a panel in preparation for the need for estimating roughly its effect as a corrosion amount. If an assumed period until the surface treatment film deteriorates and the corrosion of the atmospheric corrosion resistant steel or the coastal atmospheric corrosion resistant steel starts under these usage conditions is selected, the secular corrosion amount prediction curve is recalculated as shown in FIG. 19 in the case of JIS type atmospheric corrosion resistant steel subjected to general painting surface treatment, and as shown in FIG. 20 in the case of the JIS type atmospheric corrosion resistant steel subjected to surface treatment for atmospheric corrosion resistant steel.

The former shown in FIG. 19 is a corrosion/wear prediction curve obtained by making a calculation with the start time of corrosion of the steel material as after 25 years on the assumption that the treatment for promoting the formation of protective rust is not performed. On the other hand, the latter shown in FIG. 20 is a corrosion/wear prediction curve obtained by making a calculation with the start time of corrosion as after 25 years and simultaneously multiplying a coefficient of effect on the first-year corrosion amount A and the rust stabilization index B on the assumption that the treatment for promoting the formation of protective rust is performed. From these calculation results, under this environment, it can be determined that 100-year service life can be realized by minimum maintenance by subjecting the JIS type atmospheric corrosion resistant steel to surface treatment which promotes the formation of the protective rust.

Repainting in surface treatment for the atmospheric corrosion resistant steel is not generally expected, but in this software, to answer purposes and needs such as the realization of very long-term durability at low cost under severe corrosive environment, use of surface treatment for landscape specifications, an increase in life combined with painting, and the like, the calculation of the corrosion/wear curve when repainting is permitted is also possible. When a "Repeat" button is clicked after the number of durable years of the surface treatment film is inputted in the screen in each of FIG. 18 to FIG. 21, a panel which encourages an input of a grace period before repainting is displayed. The default is ten years, but a change is possible between zero years to 60 years. For example, when the durability of a general surface treatment film is set to 25 years and the grace period before repainting is set to five years, this software is so programmed that a corrosion/wear curve of a total of 30 years is repeated in an additional manner, and as a result, a corrosion/wear prediction curve as a standard up to 100 years may be ascertained. The result of this is shown as in FIG. 22. From FIG. 22, it can be determined that when general surface treatment is performed for the atmospheric corrosion resistant steel under these environmental conditions, 100-year service life can be realized if a design and a maintenance management policy on the assumption of repainting are made.

In the aforementioned examples of corrosion/wear prediction, calculation is made by inputting conditions as macro representatives of construction environment, but in an actual structure which has a complicated shape and extends over a wide range, environmental conditions are different from one portion of the structure to another. Accordingly, the need for improving prediction precision by ascertaining environmental conditions according to each portion of a structure, and studying a corrosion protection designing method according to each portion of the structure is pointed out.

Figure 23:
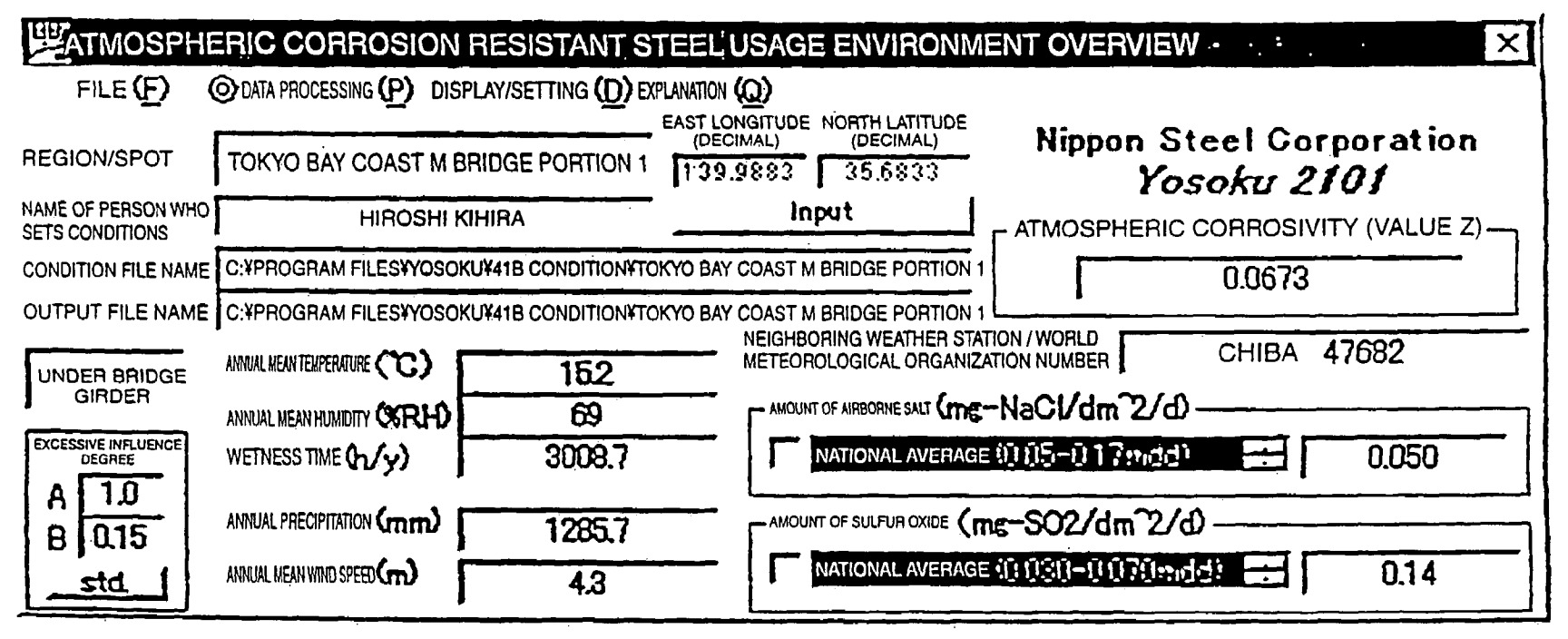

FIG. 23 is an example of conditions inputted to a panel of "Usage Environment Conditions Setting" in a portion of a structure around which the amount of airborne salt is assumed to be relatively small in a bridge structure to be constructed. Such conditions can hold in general girder surfaces which are not directly exposed to a sea wind in the bridge.

Figure 24:
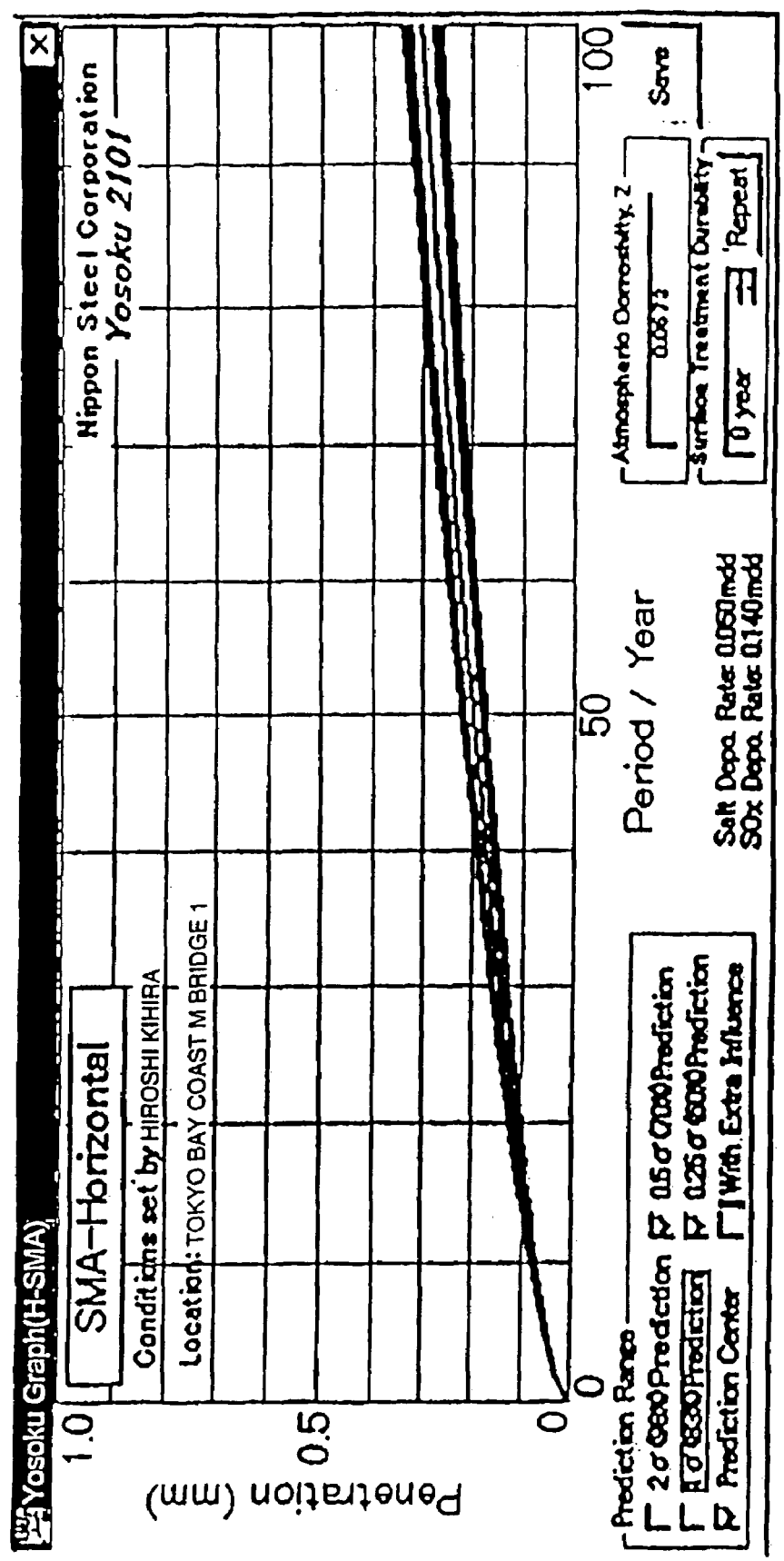
FIG. 24 is a chart showing an example of a corrosion/wear prediction curve calculated under the conditions in FIG. 23 in the portion of the structure around which the amount of airborne salt is assumed to be relatively small.

FIG. 24 is an example of a corrosion/wear prediction curve calculated under the conditions in FIG. 23 in the portion of the structure around which the amount of airborne salt is assumed to be relatively small. The precision of a prediction calculation rises by a rise in the precision of setting of environmental conditions according to each portion of a structure, so that a region up to 0.5σ is displayed. From this prediction result, it is determined that 100-year durability can be fully realized even if the bare JIS type atmospheric corrosion resistant steel is used for these general girder surfaces.

FIG. 25 is an example of conditions inputted to the panel of "Usage Environment Conditions Setting" in a portion of the structure around which the amount of airborne salt is assumed to be relatively large and the humidity is assumed to be high in the bridge structure to be constructed. Such conditions can hold in girder end portions or the like which are structurally poorly ventilated with a tendency of high humidity.

Figure 26:
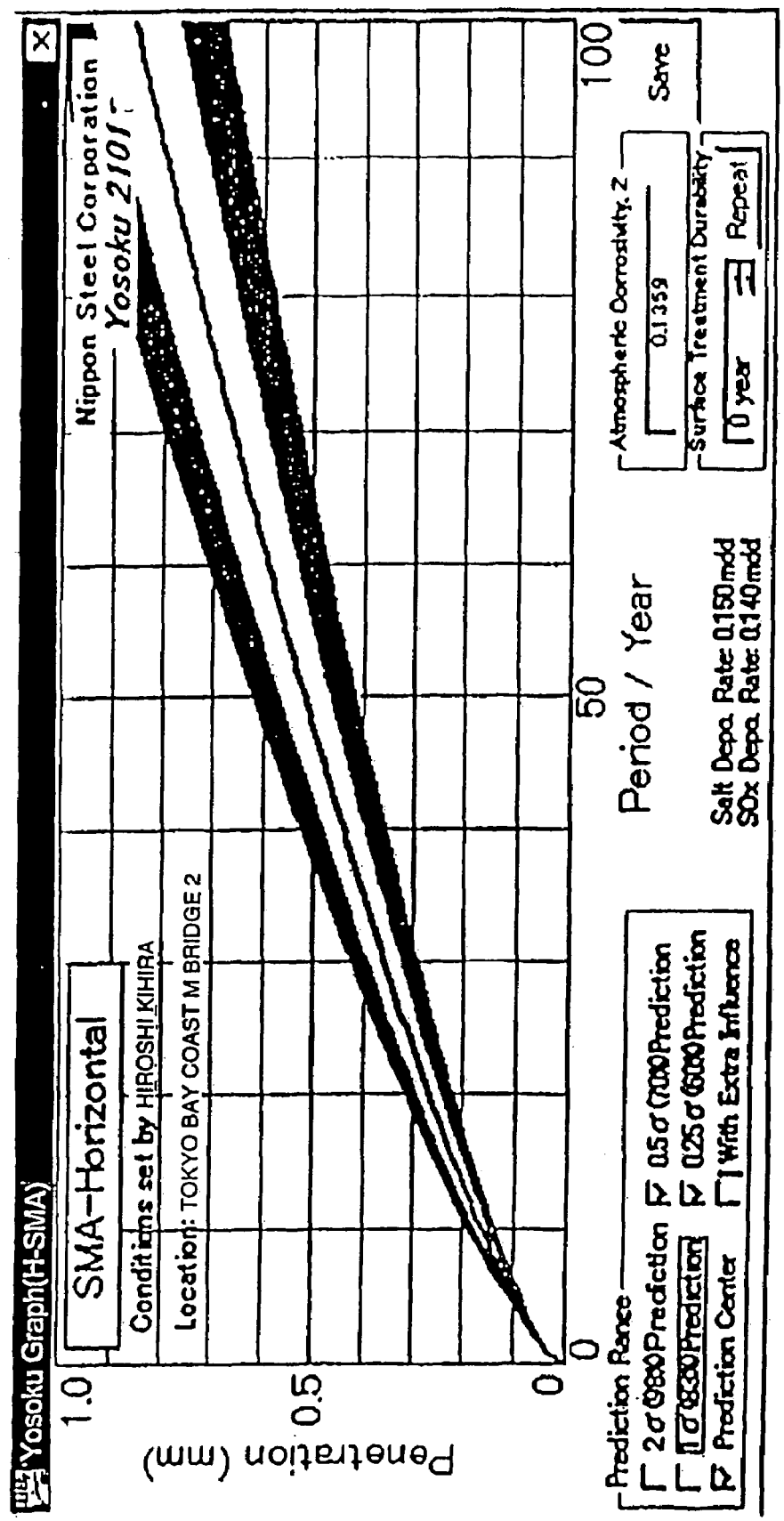
FIG. 26 is chart showing an example of a corrosion/wear prediction curve calculated under the conditions in FIG. 25 in the portion of the structure around which the amount of airborne salt is assumed to be relatively large and the humidity is assumed to be high.

FIG. 26 is an example of a corrosion/wear prediction curve calculated under the conditions in FIG. 25 in the portion of the structure around which the amount of airborne salt is assumed to be relatively large and the humidity is assumed to be high. Also in this case, the precision of setting of environmental conditions rises, so that as concerns the prediction curve, a region up to 0.5σ is displayed. From this prediction result, it turns out that even in the same construction object, the corrosive environment is sometimes locally severe, so that if a portion of the structure under the severe environment is barely used, corrosion excessively progresses, which causes a problem. There is a possibility that a minimum maintenance structure can be realized by taking some corrosion protection measure against only such a portion of the structure.

Figure 27:
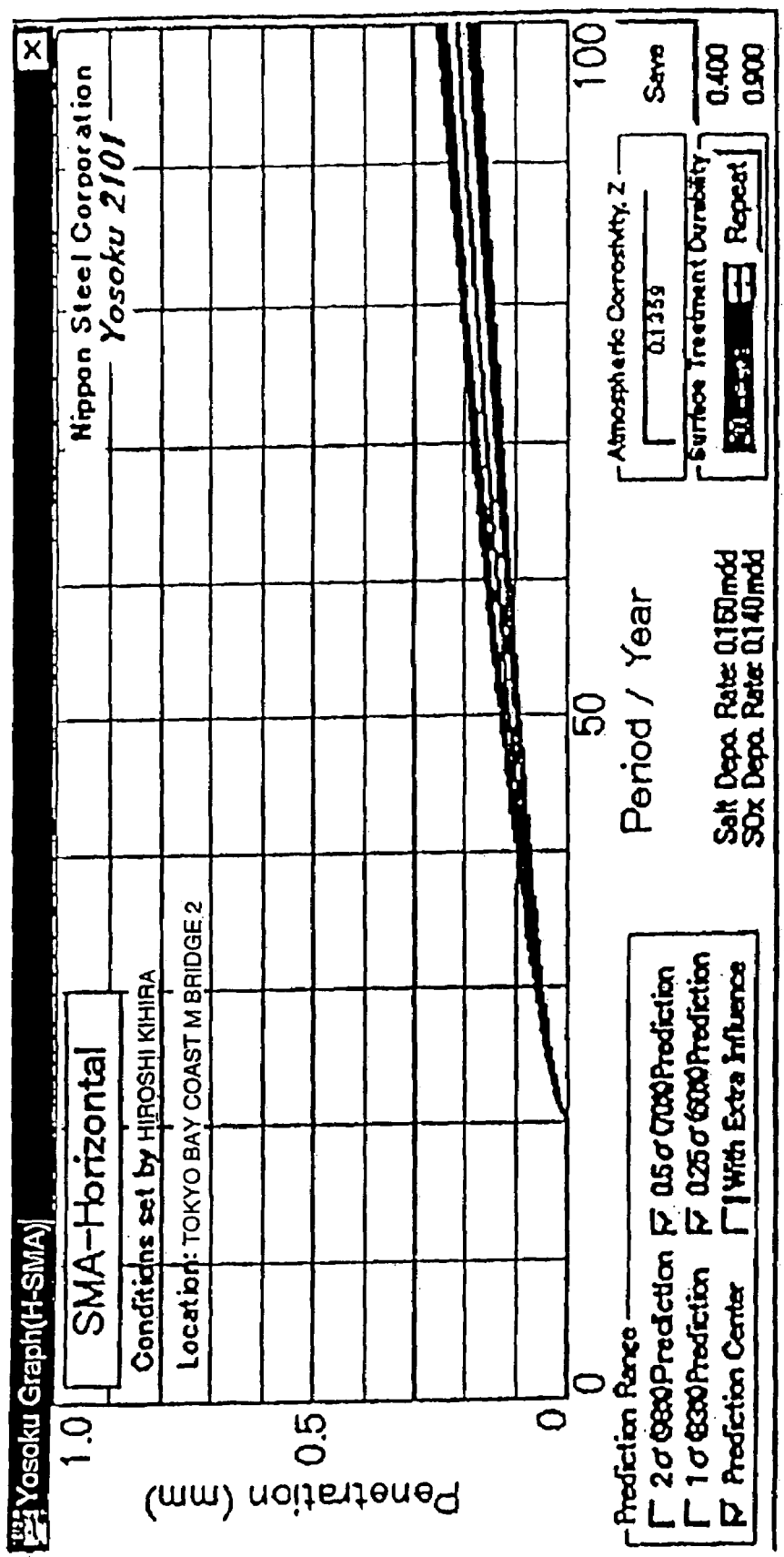
FIG. 27 is a chart showing an example of a corrosion/wear prediction curve calculated under the conditions in FIG. 25 in the portion of the structure around which the amount of airborne salt is assumed to be relatively large and the humidity is assumed to be high and which is subjected to the rust stabilization surface treatment for the atmospheric corrosion resistant steel.

FIG. 27 is an example of a corrosion/wear prediction curve calculated also under the conditions in FIG. 25 in the portion of the structure around which the amount of airborne salt is assumed to be relatively large and the humidity is assumed to be high and which is subjected to rust stabilization surface treatment for the atmospheric corrosion resistant steel. Based on this prediction result, it can be determined that very long-term durability can be realized at the lowest cost as the entire structure if only a portion of the structure under the locally severe corrosive environment is subjected to the rust stabilization surface treatment. Accordingly, it becomes possible to reflect this knowledge in the design from the beginning. Similarly, as for existing structures, it is also possible to make a prediction on future corrosion and wear on a portion-by-portion basis and draw up a maintenance management policy.

If a calculation method for predicting the long-term corrosion/wear amount of the painted atmospheric corrosion resistant steel which is implemented in the form of software as described above can be widely and generally used, is possible to (i) determine the applicability of the atmospheric corrosion resistant steel, (ii) select a steel type, (iii) select a surface treatment method, (iv) make a durable design, (v) draw up a maintenance management policy, and so on at any given construction site, which is not limited within any country, by referring to its output data. Consequently, understanding of the proper usage of the atmospheric corrosion resistant steel is spread, which contributes to an increase in the reliability of this steel material. Moreover, the provision of safe, secure and low life-cycle cost infrastructure is furthered. Also, by a comparison with the predicted calculation result, research and development on new atmospheric corrosion resistant steel materials and the surface treatment and maintenance management method therefor are made more efficient, and moreover it is needless to say that the predicted calculation result can be effectively utilized for the setting of a new development goal. Its utilization inevitably leads to a great increase in the efficiency of a business method concerning the atmospheric corrosion resistant steel and the surface treatment therefor.

Moreover, the following business form can be realized by using software capable of carrying out the method according to the present invention.

First, in the stage of planning a steel structure to which the atmospheric corrosion resistant steel is applied (the stage of selecting a steel type), it is possible to plan the type of steel applied to the steel structure through the steps of: calculating a predicted corrosion amount of one type or more than one type of atmospheric corrosion resistant steel as a candidate based on numerical values obtained by actually measuring or estimating environmental data including an annual mean temperature, humidity, precipitation, wind direction/speed, airborne salt amount, sulfur oxide amount, and so on in a planned location for use where a user plans to use the atmospheric corrosion resistant steel by the method of the present invention; and comparing the predicted corrosion amount and a design permissible corrosion amount in a design life period. In other words, it is possible to select a steel type through the calculation of a predicted corrosion amount of the aforementioned each atmospheric corrosion resistant steel with extrinsic corrosion information including weather observation data, an amount of airborne salt, and an amount of sulfur oxide in the planned location for use where the atmospheric corrosion resistant steel is to be used, and intrinsic corrosion information on components of one or more than one type of atmospheric corrosion resistant steel planned to be used, and the comparison of the aforementioned predicted corrosion amount and the design permissible corrosion amount in the design life period.

In this determination of applicability, generally, when the predicted corrosion amount of the atmospheric corrosion resistant steel is equal to or smaller than the permissible corrosion amount in the comparison between the predicted corrosion amount and the permissible corrosion amount, this atmospheric corrosion resistant steel is regarded as an applicable steel type, but in some cases, for example, when a large amount of thawing salt is sprayed to prevent the road surface from freezing, excessive influence factors need to be taken into consideration.

In such case, it is suitable that in the comparison between the predicted corrosion amount and the permissible corrosion amount, the difference between them is set to be a given specified amount or more according to the excessive influence factors, and it is preferable to incorporate this in the exemplary predicting method according to the present invention as a correction for rust stabilization factors.

It is preferable that this planning method or selection method further includes the steps of: regarding a steel type whose predicted corrosion amount exceeds the permissible corrosion amount, recalculating a predicted corrosion amount after adding a corrosion protection method and/or a maintenance management method capable of reducing the predicted corrosion amount to the permissible corrosion amount or less; and disclosing an expected cost and an expected life to a user when one type or more than one type of atmospheric corrosion resistant steel as a candidate is applied to a spot and a portion of a structure to be used by the user. Namely, regarding the steel type whose predicted corrosion amount exceeds the permissible corrosion amount, it is preferable to calculate a predicted corrosion amount when at least one type of method selected from the group consisting of a corrosion protection method and a maintenance management method for reducing the predicted corrosion amount. Moreover, it is preferable to obtain an expected cost and an expected life when the one or more than one type of atmospheric corrosion resistant steel is used in the planned location for use. This is because the cost including surface treatment and the like, life, and so on can be also simultaneously considered.

Next, in the maintenance management of the steel structure, it is possible to calculate first-year corrosion amounts $A_V$ and $A_H$ based on actual measurement of corrosion losses after a lapse of any given period of time, and based on the predicted corrosion amount recalculated from the actually measured first-year corrosion amounts by the method of present invention, to determine a more appropriate future maintenance management policy. In other words, it is possible to calculate actually measured first-year corrosion amounts of a vertical exposure member and a horizontal exposure member made of an atmospheric corrosion resistant steel respectively based on measurement results of corrosion losses in any given period of time of the vertical exposure member and the horizontal exposure member made of the atmospheric corrosion resistant steel, calculate a predicted corrosion amount of the atmospheric corrosion resistant steel with extrinsic information including weather observation data, an amount of airborne salt, and an amount of sulfur oxide in a planned location for use where the atmospheric corrosion resistant steel is to be used, intrinsic corrosion information on components of the atmospheric corrosion resistant steel, and the respective actually measured first-year corrosion amounts, and determine the maintenance management policy based on the predicted corrosion amount.

In this case, it is preferable that the recalculation is coefficient correction in the corrosivity index Z. Namely, it is preferable to calculate the corrosivity index Z with the under mentioned equation (Eq. 6) when the predicted corrosion amount is calculated.

When an actual measured value exceeds a predicted value with regard to $A_V$ and/or $A_H$, it is preferable to adopt a maintenance management policy in which the future predicted corrosion amount becomes equal to or less than a predicted corrosion amount at the beginning of planing. More specifically, when at least one of the actually measured first-year corrosion amounts of the vertical exposure member and the horizontal exposure member made of the atmospheric corrosion resistant steel exceeds the predicted corrosion amount, it is preferable to adopt such a maintenance management policy that the predicted corrosion amount becomes smaller than a value at the beginning of planning. However, it is preferable to determine the amount of an excess when the management policy is actually changed in consideration of the absolute value of the corrosion amount and so on.

A more appropriate maintenance management policy includes the change of a portion of a structure subjected to one type or more than one type of operation out of inspection, repair, and cleaning and/or the timing of performing the operation from originally planed ones. It should be noted that the maintenance management policy is not limited to the above.

Figure 28:
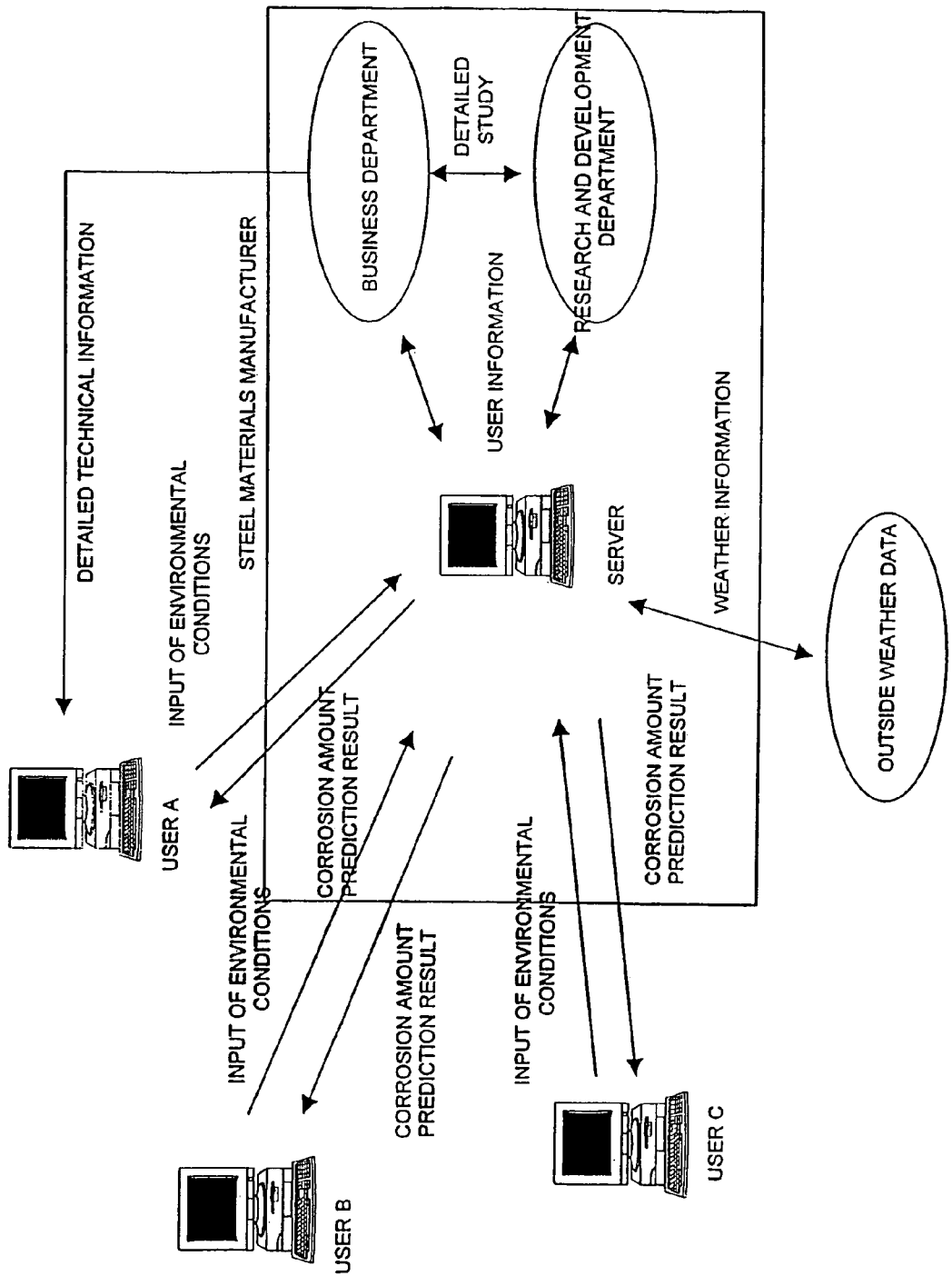
FIG. 28 is a diagram schematically showing an example of a method for providing information on the atmospheric corrosion resistant steel based on the method for predicting corrosion according to the embodiment of the present invention.

Moreover, in an exemplary method for providing information on the atmospheric corrosion resistant steel, as an example thereof is shown in FIG. 28, a method for providing information on an atmospheric corrosion resistant steel, including the steps of: a user accessing a server capable of performing the method of the present invention via an electric communication line such as the Internet and inputting environmental data including an annual mean temperature, a humidity, a precipitation, a wind direction/speed, an amount of airborne salt, and an amount of sulfur oxide in a spot and a portion of a structure to which the user plans to apply the atmospheric corrosion resistant steel, based on actually measured or estimated numerical values; calculating a predicted corrosion amount of one type or more than one type of atmospheric corrosion resistant steel as a candidate based on the input and the selection of a steel type which the user plans to use according to the method of the present invention; and displaying a result of the calculation in a terminal of the user via the electric communication line such as the Internet, becomes possible. In other words, the provision of information including the steps of: a user accessing a server for calculating a predicted corrosion amount of an atmospheric corrosion resistant steel with environmental data including weather observation data, an amount of airborne salt, and an amount of sulfur oxide, and intrinsic corrosion information on components of the atmospheric corrosion resistant steel from a terminal device via an electric communication line; the user inputting environmental data including weather observation data, an amount of airborne salt, and an amount of sulfur oxide in a planned location for use where an atmospheric corrosion resistant steel is to be used from the terminal device to the server; the user permitting the server to recognize intrinsic corrosion information on components of one or more than one type of atmospheric corrosion resistant steel planned to be used from the terminal device; the server calculating a predicted corrosion amount of each of the atmospheric corrosion resistant steels based on the environmental data and the intrinsic corrosion information; the server transmitting the predicted corrosion amount to the terminal device via the electric communication line; and the terminal device outputting the predicted corrosion amount from the terminal device, becomes possible.

It is one of preferable embodiments that such information is provided as part of a homepage of a steel materials manufacturer. By providing such information, a user can investigate whether an atmospheric corrosion resistant steel can be actually used in a spot and a portion of a structure to which the user plans to apply the atmospheric corrosion resistant steel on the Internet. As a result, this becomes very useful information disclosure to diffuse the atmospheric corrosion resistant steel.

It is preferable that the user can select a steel type whose predicted corrosion amount is to be calculated by preparing a window in which the environmental data on the spot and the portion of the structure to which the user plans to apply the atmospheric corrosion resistant steel is inputted for access from the user and displaying steel types which the steel materials manufacturer can provide by a menu selection method in this window. This improves user-friendliness and facilitates the arrangement of data when the data is stored in the server.

Further, the environmental data inputted by the user is preferably a mean temperature, humidity, wind direction/speed, and so on actually measured in the spot and the portion of the structure to which the user plans to apply the atmospheric corrosion resistant steel in view of the fact that the aforementioned data provides the steel materials manufacturer with useful information as data on calculation precision of the predicted corrosion amount and steel materials environment.

However, on the other hand, it is naturally assumed that there are many users which have access without the aforementioned preparation, and hence it is preferable for convenience of the user that the step of acquiring part or all of environmental data necessary for calculation in a manner other than the aforementioned input is further included. In other words, it is preferable that the step of the server acquiring at least part of elements constituting the environmental data in a manner other than the input by the user is further included. For example, such an embodiment that clicking a location for use of a steel material on a map links to a database of the Meteorological Agency or the like and thereby necessary environmental data can be retrieved or calculated is preferable.

Furthermore, since it is open to an unspecified number of users, it is preferable that an access right in the server is hierarchized, and that an access right for a user ID to access the server is set according to a usage record of the atmospheric corrosion resistant steel of the user.

If the environmental data inputted by the user is stored in the server and can be seen from the server administration side, it becomes possible to determine a business counterpart based on user IDs which got access to the server or the frequency of access by using the data, analyze the environmental data inputted by the user and stored and accumulated in the server, and based on a result thereof, enlarge the environment to which existing steel types are applied and perform research and development on new steel types.

Additionally, if the user is provided with further detailed information in addition to calculation results obtained by access from the user to the server when there is a request from the user and/or when special consideration to the inputted environment is necessary, it is more preferable in terms of the user's convenience and prevention of wrong use of the steel type.

In this case, it is efficient and desirable to transfer the detailed information to a terminal installed in the user's nearest business base via an electric communication line such as the Internet. The nearest business base includes a place of the user to which a person in charge of business goes. Namely, the detailed information may be transferred to the terminal installed in the user's nearest business base or may be transferred to a portable terminal brought into the place of the user.

In a situation of a business operation in front of the user, in the study of application of an atmospheric corrosion resistant steel to a spot and a portion of a structure to which the user plans to apply the atmospheric corrosion resistant steel, a form of business for an atmospheric corrosion resistant steel including the steps of: a person in charge of business inputting environmental data including an annual mean temperature, a humidity, a precipitation, a wind direction/speed, an amount of airborne salt, and an amount of sulfur oxide in the spot and the portion of the structure to which the user plans to apply the atmospheric corrosion resistant steel based on actually measured or estimated numerical values to a computer capable of executing the method of the present invention via an electric communication line such as the Internet or in a stand-alone system; calculating a predicted corrosion amount of one type or more than one type of atmospheric corrosion resistant steel as a candidate by the method of the present invention according to the aforementioned input and the selection of the steel type which the user plans to use; and presenting a result of the calculation to the user, becomes possible.

In other words, a business for an atmospheric corrosion resistant steel, including the steps of: a person in charge of business inputting extrinsic corrosion information including weather observation data, an amount of airborne salt, and an amount of sulfur oxide in a planned location for use where a customer plans to use an atmospheric corrosion resistant steel to an electronic calculator for calculating a predicted corrosion amount of an atmospheric corrosion resistant steel with extrinsic corrosion information including weather observation data, an amount of airborne salt, and an amount of sulfur oxide and intrinsic corrosion information on components of the atmospheric corrosion resistant steel; the person in charge of business permitting the electronic calculator to recognize intrinsic corrosion information on components of one or more than one type of atmospheric corrosion resistant steel which the customer plans to use; the electronic calculator calculating a predicted corrosion amount of each of the atmospheric corrosion resistant steels;

and the person in charge of business presenting a result of the calculation by the electronic calculator to the customer becomes possible.

Also in this case, it is preferable for convenience that the step of acquiring or calculating part or all of environmental data necessary for calculation in a manner other than the aforementioned input is further included. Moreover, regarding a steel type whose predicted corrosion amount exceeds a permissible corrosion amount, it is very desirable that the step of recalculating a predicted corrosion amount after a corrosion protection method and/or a maintenance management method such as can reduce the predicted corrosion amount to the permissible corrosion amount or less is added and the step of disclosing an expected cost and an expected life when one type or more than one type of atmospheric corrosion resistant steel as a candidate is applied to a spot and a portion of a structure in which the user uses it, are further includes, since the cost including surface treatment and so on, the life, and the like can be studied at the same time.

Also in this business form, a terminal capable of performing the calculation by the method of the present invention may be located in a business department or a person in charge of business may take such a portable terminal to a place of the user. Preferably, if access to weather data and so on disclosed by the Meteorological Agency from this terminal is possible, a concrete study based on data can be made on the spot during consultation on the selection of a steel material even when the user does not keep data such as temperature on hand.

According to this exemplary business method according to the present invention, not only the business operation can be made more efficient, but also a large merit that steel types as candidates can be promptly and quantitatively compared can be provided to the user. Besides, this prompt provision of quantitative data enhances understanding of the added value of a steel material called atmosphere corrosion resistance which conventionally has many uncertain factors and leads to further diffusion of the atmospheric corrosion resistant steel.

INDUSTRIAL APPLICABILITY

According to a method of the present invention, the amount of corrosion in a service life of several decades can be predicted with high precision even based on limited actual measurement data such as an exposure test. Moreover, it is also easy to incorporate a corrosion protection method and a maintenance management method therein.

The present invention can make various operations such as judgment on the applicability of an atmospheric corrosion resistant steel, selection of a material, durability design, judgement on the applicability of surface treatment and selection of its type, and creation of a maintenance management policy, which hitherto rely on a long-term exposure test, more precise and more efficient. Moreover, the present invention can reduce the cost of the business operation of the atmospheric corrosion resistant steel. Accordingly, the present invention can contribute to a rise in the competitiveness of the atmospheric corrosion resistant steel.

Conventionally, the judgment on the applicability has been made only by the amount of airborne salt, whereby in some region, the application of the atmospheric corrosion resistant steel is withheld even though it is a region where maintenance and management costs can be originally reduced by using the atmospheric corrosion resistant steel, which causes an increase in construction client's maintenance and management costs. Contrary to this, repair costs are sometimes caused since abnormal corrosion unexpectedly occurs due to high humidity and temperature or the like even though the amount of airborne salt is small. According to the present invention, it is possible to avoid such situations beforehand.

Such avoidance of problems prevents troubles when the atmospheric corrosion resistant steel is used which are probably caused by the existence of uncertain factors on the environment side. Accordingly, the present invention fulfills a role in maintaining an infrastructure safely and securely. It becomes possible to design a structure manufactured of an atmospheric corrosion resistant steel having a more than 100 year-service life by a combination of these series of long-term corrosion/wear predictions and various kinds of corrosion protection methods based on obtained calculation results. Consequently, the realization of minimum maintenance of an infrastructure is enhanced.

The invention claimed is:

1. A method comprising:
    measuring or obtaining TOW, an annual wetness time (h) in a location;
    measuring or obtaining W, an annual mean wind speed (m/sec.) in the location;
    measuring or obtaining C, an airborne salt amount (mdd) in the location;
    measuring or obtaining S, a sulfur oxide amount (mdd) in the location;
    measuring or obtaining T, an annual mean temperature (K) in the location;
    determining a corrosivity index Z of an atmospheric corrosion resistant steel at the location where the atmospheric corrosion resistant steel is to be used;
    determining a corrosion amount of the atmospheric corrosion resistant steel using the corrosivity index Z; and
    selecting a steel type for a steel structure, or designing or maintaining the steel structure based on the determined corrosion amount,
    wherein the corrosivity index Z is determined using the following equation $$Z = \alpha \cdot TOW \cdot \exp(-\kappa \cdot W) \cdot \frac{C + \delta \cdot S}{1 + \varepsilon \cdot C \cdot S} \cdot \exp\left(\frac{-E_a}{R \cdot T}\right)$$

where Ea is activation energy (J/mol) of a corrosion reaction of the atmospheric corrosion resistant steel, R is a gas constant (J/K(K·mol)), α is a coefficient constant, and κ, δ, and ε are influence degree constants.

2. The method according to claim 1, further comprising a substep of determining a corrosion amount accumulated over time of the atmospheric corrosion resistant steel by estimating a first-year corrosion amount and a rust stabilization index of the atmospheric corrosion resistant steel from the corrosivity index Z.

3. The method according to claim 1, further comprising a substep of estimating a first-year corrosion amount $A_V$ of a vertical exposure member and a first-year corrosion amount $A_H$ of a horizontal exposure member from the corrosivity index Z by a quadratic regression analysis.

4. The method according to claim 3, further comprising finding a relational expression based on the following equations:

$A_V(\mu m) = 37.60 Z^2 + 74.44 Z + 7.37$ $(p = 7.64 \times 10^{-39})$ $A_H(\mu m) = -24.16 Z^2 + 182.19 Z + 4.05$ $(p = 1.12 \times 10^{-23})$.

5. The method according to claim 3, further comprising determining a range of variations by multiplying estimated values of the first-year corrosion amounts $A_V$ and $A_H$ by each of respective constants which correspond to an upper limit and a lower limit of said range of variations.

6. The method according to claim 5, wherein each upper or lower limit of the range of variations is determined by using one of:

taking an upper limit $A^{Upper}_V$ of a range of the first-year corrosion amount $A_V$ as the following equation: $A_V^{Upper}=1.7A_V$;

taking a lower limit $A^{Lower}_V$ of the range of the first-year corrosion amount $A_V$ as the following equation:

$$A_V^{Lower} = \frac{1}{1.7}A_V;$$

taking an upper limit $A^{Upper}_H$ of a range of the first-year corrosion amount $A_H$ as the following equation: $A_H^{Upper}=1.7A_H$; and taking a lower limit $A^{Lower}_H$ of the range of the first-year corrosion amount $A_H$ as the following equation:

$$A_H^{Lower} = \frac{1}{1.7}A_H.$$

7. The method according to claim 3, further comprising, based on the first-year corrosion amounts $A_V$ and $A_H$ and a distribution function of a rust stabilization index:

taking an upper limit of a region where 80% or more of measurement points are distributed as a natural upper rust stabilization index or as an excessive influence rust stabilization index obtained by adding a value according to the degree of excessive influence to the natural upper rust stabilization index;

taking a lower limit of the region where 80% or more of the measurement points are distributed as a natural lower rust stabilization index; and taking a value obtained by adding 0.15 to the natural upper rust stabilization index as the excessive influence rust stabilization index.

8. The method according to claim 1, wherein the determined corrosion amount is used to select a steel type for a steel structure.

9. The method according to claim 1, wherein the determined corrosion amount is used to design a steel structure.

10. The method according to claim 1, wherein the determined corrosion amount is used to maintain a steel structure.

* * * * *

UNITED STATES PATENT AND TRADEMARK OFFICE
CERTIFICATE OF CORRECTION

| | | |
|---|---|---|
| PATENT NO. | : 7,231,318 B2 | Page 1 of 1 |
| APPLICATION NO. | : 10/483504 | |
| DATED | : June 12, 2007 | |
| INVENTOR(S) | : Hiroshi Kihira et al. | |

It is certified that error appears in the above-identified patent and that said Letters Patent is hereby corrected as shown below:

ON COVER PAGE:

(54) Title,

"Method For Predicting Degree Of Corrosion Of Weather-Resistant Steel" should be --Method For Predicting Amount Of Corrosion Of Atmospheric Corrosion Resistant Steel--

Signed and Sealed this

Twenty-third Day of December, 2008

JON W. DUDAS
*Director of the United States Patent and Trademark Office*

UNITED STATES PATENT AND TRADEMARK OFFICE
CERTIFICATE OF CORRECTION

PATENT NO. : 7,231,318 B2  Page 1 of 1
APPLICATION NO. : 10/483504
DATED : June 12, 2007
INVENTOR(S) : Hiroshi Kihira et al.

It is certified that error appears in the above-identified patent and that said Letters Patent is hereby corrected as shown below:

ON COVER PAGE:

(54) and Column 1, lines 1-3 Title,

"Method For Predicting Degree Of Corrosion Of Weather-Resistant Steel" should be --Method For Predicting Amount Of Corrosion Of Atmospheric Corrosion Resistant Steel--

This certificate supersedes the Certificate of Correction issued December 23, 2008.

Signed and Sealed this

Twenty-seventh Day of January, 2009

JOHN DOLL
*Acting Director of the United States Patent and Trademark Office*